United States Patent
Menon et al.

(10) Patent No.: US 12,262,884 B2
(45) Date of Patent: Apr. 1, 2025

(54) MULTIPURPOSE MEDICAL DEVICE

(71) Applicant: Dignity Health, San Francisco, CA (US)

(72) Inventors: Ram Kumar Menon, Kerala (IN); Brian P Kelly, Tempe, AZ (US); Anna Sawa, Chandler, AZ (US)

(73) Assignee: DIGNITY HEALTH, San Francisco, CA (US)

( * ) Notice: Subject to any disclaimer, the term of this patent is extended or adjusted under 35 U.S.C. 154(b) by 273 days.

(21) Appl. No.: 16/754,069

(22) PCT Filed: Oct. 5, 2018

(86) PCT No.: PCT/US2018/054716
§ 371 (c)(1),
(2) Date: Apr. 6, 2020

(87) PCT Pub. No.: WO2019/071203
PCT Pub. Date: Apr. 11, 2019

(65) Prior Publication Data
US 2020/0323524 A1 Oct. 15, 2020

Related U.S. Application Data

(60) Provisional application No. 62/568,363, filed on Oct. 5, 2017.

(51) Int. Cl.
*A61B 17/02* (2006.01)
*A61B 17/00* (2006.01)
*A61B 90/00* (2016.01)

(52) U.S. Cl.
CPC ........ *A61B 17/0218* (2013.01); *A61B 17/025* (2013.01); *A61B 2017/00022* (2013.01);
(Continued)

(58) Field of Classification Search
CPC ... A61B 17/02; A61B 17/0218; A61B 17/025; A61B 17/34; A61B 17/3403;
(Continued)

(56) References Cited

U.S. PATENT DOCUMENTS

| 5,342,385 A | 8/1994 | Norelli |
| 8,467,844 B2 | 6/2013 | Rea |

(Continued)

FOREIGN PATENT DOCUMENTS

JP H1183420 A 3/1999

OTHER PUBLICATIONS

INOMED. Dynamic Continuous Mapping of the Corticospinal Tract. Brochure. Updated Dec. 2015. 4 pages.
(Continued)

*Primary Examiner* — Christopher J Beccia
(74) *Attorney, Agent, or Firm* — QUARLES & BRADY LLP

(57) ABSTRACT

A multipurpose medical device and a method of performing a medical procedure using the device are provided. The device can include a handle, a body, a suction system, a sensor, and an indicator. The body can be operatively coupled to the handle and can include a lumen extending through a length of the body, and at least a portion of the body is configured to operate as a retractor during the medical procedure. The suction system can include a suction channel disposed within the lumen. The sensor can be coupled to the body and can be configured to sense a retraction force against the body during the medical procedure. The indicator can be configured to provide feedback to the user based on the sensed retraction force.

20 Claims, 15 Drawing Sheets

(52) U.S. Cl.
CPC .............. *A61B 2017/00039* (2013.01); *A61B 2017/00128* (2013.01); *A61B 2017/00557* (2013.01); *A61B 2090/064* (2016.02); *A61B 2090/065* (2016.02); *A61B 2217/005* (2013.01); *A61B 2217/007* (2013.01)

(58) Field of Classification Search
CPC ......... A61B 34/00; A61B 34/20; A61B 34/23; A61B 34/70; A61B 1/32; A61B 90/00
See application file for complete search history.

(56) References Cited

U.S. PATENT DOCUMENTS

| | | | |
|---|---|---|---|
| 9,326,757 B2 | 5/2016 | Ravikumar | |
| 9,636,096 B1 | 5/2017 | Heaton, II | |
| 2004/0143164 A1* | 7/2004 | Suddaby | A61B 17/0218 600/210 |
| 2008/0081951 A1 | 4/2008 | Frasier | |
| 2008/0103519 A1 | 5/2008 | Bonutti | |
| 2010/0145337 A1* | 6/2010 | Janna | A61B 17/1707 606/86 R |
| 2011/0092775 A1 | 4/2011 | Deshmukh | |
| 2011/0190588 A1* | 8/2011 | McKay | A61B 17/0206 600/202 |
| 2013/0053979 A1 | 2/2013 | Leydet et al. | |
| 2014/0275792 A1 | 9/2014 | Hawkins | |
| 2015/0216478 A1* | 8/2015 | Kaula | A61B 17/00 600/546 |
| 2016/0008026 A1* | 1/2016 | Elayaperumal | A61B 5/01 600/549 |
| 2017/0265890 A1* | 9/2017 | Page | A61B 17/0218 |

OTHER PUBLICATIONS

Raabe, A., et al. "Continuous dynamic mapping of the corticospinal tract during surgery of motor eloquent brain tumors: evaluation of a new method." Journal of Neurosurgery 120.5 (2014): 1015-1024.
Schucht, P., et al. "A review of monopolar motor mapping and a comprehensive guide to continuous dynamic motor mapping for resection of motor eloquent brain tumors." Neurochirurgie 63.3 (2017): 175-180.
European Patent Office. Extended European Search Report for application 18864761.4. Mailed on May 31, 2021. 10 pages.
Bolotin, G., et al. (2007). A novel instrumented retractor to monitor tissue-disruptive forces during lateral thoracotomy. The Journal of thoracic and cardiovascular surgery (vol. 133).
Cristofolini, L., et al. (1997). Comparison of Uniaxial and Triaxial Rosette Gages for Strain Measurement in the Femur. Experimental Mechanics (vol. 37).
Freeman, A. L., et al. (2012). Validation of an improved method to calculate the orientation and magnitude of pedicle screw bending moments. Journal of Biomechanical Engineering, 134(10), [104502].
Gan, L. S., et al. "Quantification of forces during a neurosurgical procedure: a pilot study." World neurosurgery 84.2 (2015): 537-548.
International Searching Authority, International Search Report and Written Opinion for application PCT/US2018/054716. Mailed on Jan. 2, 2019.
Maddahi, Y., et al. (2016). Real-time measurement of tool-tissue interaction forces in neurosurgery: Quantification and analysis. In 2016 IEEE International Conference on Advanced Intelligent Mechatronics (AIM) (pp. 1405-1410).
Marcus, H. J., et al. (2014). Forces Exerted during Microneurosurgery: A Cadaver Study. The international journal of medical robotics + computer assisted surgery: MRCAS (vol. 10).
Menciassi, A. et al. "Force sensing microinstrument for measuring tissue properties and pulse in microsurgery," IEEE/ASME Trans. Mechatronics, vol. 8, No. 1, pp. 10-17, Mar. 2003.
KYOWA. Resistance Change of Strain Gage Bonded to Curved Surface. (n.d.). Retrieved Apr. 19, 2018, from http://www.kyowa-ei.us/eng/technical/notes/technical_note/resistance_change.html.
Tang, B., et al. (2005). Analysis of errors enacted by surgical trainees during skills training courses. Surgery, 138(1), 14-20.
Trejos, A. L., et al. (2013). The application of force sensing to skills assessment in Minimally Invasive Surgery. In 2013 IEEE International Conference on Robotics and Automation (pp. 4370-4375).
Trejos, A. L., et al. (2014). A sterilizable force-sensing instrument for laparoscopic surgery. In 5th IEEE RAS/EMBS International Conference on Biomedical Robotics and Biomechatronics (pp. 157-162).
Wanzel KR, et al. Teaching the surgical craft: From selection to certification. Curr Probl Surg. 2002;39:573-659.
Watanabe, T., et al. (2016). Force-Sensing Silicone Retractor for Attachment to Surgical Suction Pipes. Sensors (vol. 16).
Watanabe, T., et al. (2017). A Force-Visualized Silicone Retractor Attachable to Surgical Suction Pipes. Sensors (vol. 17).
Zareinia, K., et al. (2016). A Force-Sensing Bipolar Forceps to Quantify Tool-Tissue Interaction Forces in Microsurgery. IEEE/ASME Transactions on Mechatronics, 21(5), 2365-2377.
Neurovision Medical Products. DryTouch Disposable Monopolar Suction Stimulator Probes Product Information Brochure. 2014. 3 pages. Available online at http://www.neurovisionmedical.com/IFU/i21_Rev-C.pdf. Version accessed at https://web.archive.org/web/20160806220314/http://neurovisionmedical.com:80/IFU/i21_Rev-C.pdf.
Neurovision Medical. Traditional 510k—Suction Stimulator Probe. Jun. 28, 2011. 5 pages.

* cited by examiner

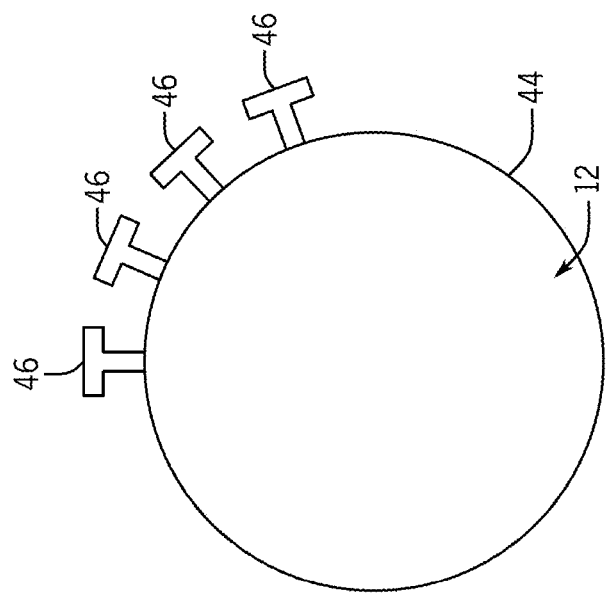
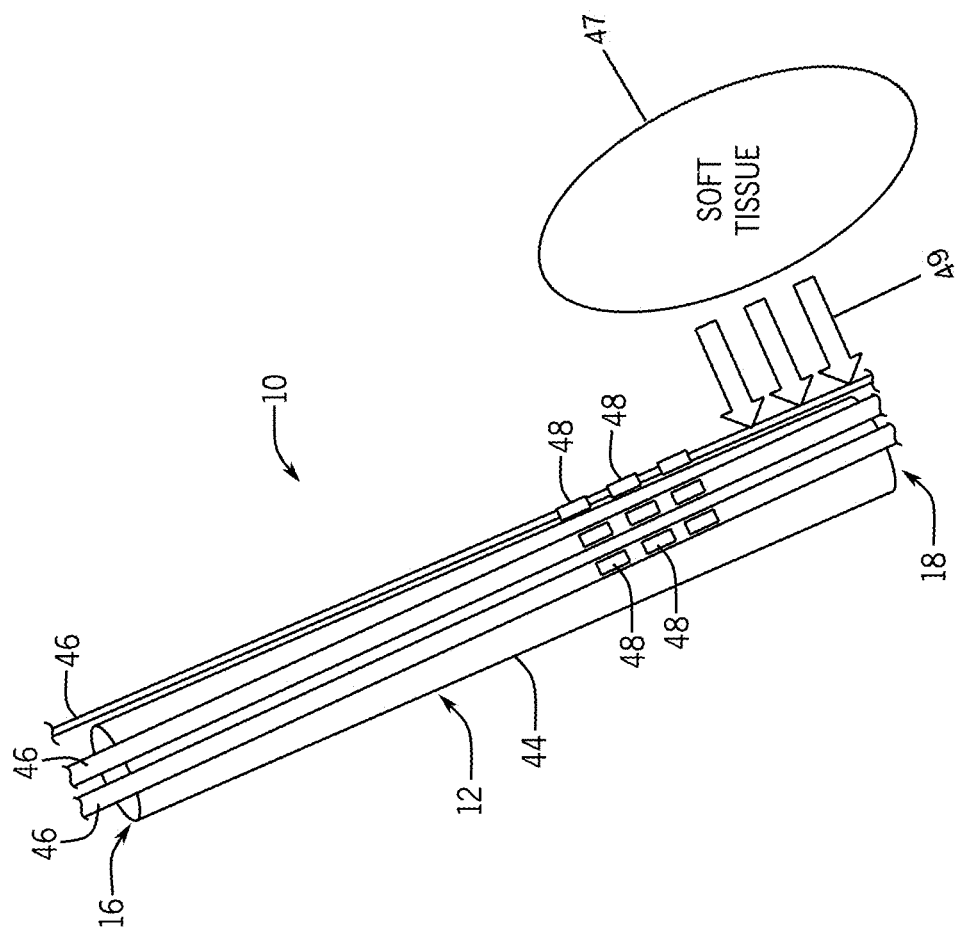
FIG. 12B
FIG. 12A

MULTIPURPOSE MEDICAL DEVICE

RELATED APPLICATIONS

This application represents the U.S. National Stage of International Application No. PCT/US2018/054716 filed Oct. 5, 2018 which claims priority under 35 U.S.C. § 119 to U.S. Provisional Patent Application No. 62/568,363 filed on Oct. 5, 2017, the entire contents of which is incorporated herein by reference.

FIELD

Some embodiments provided herein are generally related to a multi-purpose medical device and may be specifically related to a medical device that provides a plurality of functionalities, including but not limited to retraction, suction, force sensing, user feedback, lighting, nerve stimulation, and/or irrigation.

BACKGROUND

Conventional medical devices used in complex procedures, such as cranial, spinal, and peripheral nerve surgeries often exhibit significant shortcomings for the healthcare providers that use these devices. For example, some conventional devices, such as conventional suction devices, may be used as both a platform for providing suction as well as for providing retraction of sensitive tissues, such as brain or nerve tissue. However, these conventional suction devices may inadvertently damage these delicate tissues because the level of retraction force exerted by the healthcare provider may exceed what is tolerable by the tissue. For example, in neurosurgery, excessive force may lead to bleeding, post-operative pain, or irreparable injury. Understanding a tolerable amount of force exertion must be learned by experience through case studies and hands-on training. Yet in hands-on training environments, trainers can only provide subjective or qualitative feedback to trainees. As such, excessive force is one of the main errors caused by surgical trainees.

Moreover, healthcare providers may use multiple instruments during these complex procedures, such as forceps, retractors, scalpels, suction, etc. Changing between instruments requires time and can cause loss of concentration. Increased swapping between instruments can also lead to increased risk of infection and clutter in the procedure room. Furthermore, to reduce switching between tools, healthcare providers will often use a tool for functions other than its specified function. For example, surgeons will often use surgical tools as retractors because it is more convenient than using separate retractors. In one specific example, a surgeon may use a surgical suction pipe simultaneously to retract tissue and remove fluids. However, there is no way to monitor the force production of such surgical tools against tissues. This lack of quantifiable feedback may lead excessive force being used, which can cause post-surgical pain or complications.

Thus, there is a demonstrated need for developing a multi-purpose device that can provide a plurality of functionalities, including force sensing, to improve actions on the part of healthcare providers performing these complex procedures.

SUMMARY

Some embodiments include a multipurpose medical device configured to be used by a user during a medical procedure. The device can include a handle, a body, a suction system, a sensor, and an indicator. The body can be operatively coupled to the handle and can include a lumen extending through a length of the body, and at least a portion of the body is configured to operate as a retractor during the medical procedure. The suction system can include a suction channel disposed within the lumen. The sensor can be coupled to the body and can be configured to sense a retraction force against the body during the medical procedure. The indicator can be configured to provide feedback to the user based on the sensed retraction force.

Some embodiments provide a method of performing a medical procedure within a surgical field. The method can include providing a multipurpose medical device comprising a body configured to operate as a retractor, an inner surface of the body comprising a lumen, a suction system at least partially disposed within the lumen, and a sensing system at least partially supported by the body. The method can also include positioning the device within the surgical field and retracting one or more tissues within the surgical field using the device. The method can further include sensing force exerted against the device during retraction using a sensor of the sensing system and providing an indication via an indicator of the sensing system if the sensed force exceeds a predetermined threshold.

Additional objectives, advantages and novel features will be set forth in the description which follows or will become apparent to those skilled in the art upon examination of the drawings and detailed description which follows.

BRIEF DESCRIPTION OF THE DRAWINGS

FIG. 12A illustrates a perspective view of a body of a multipurpose medical device according to some embodiments. FIG. 12B illustrates a cross-sectional view of the multipurpose medical device of FIG. 12A.

Corresponding reference characters indicate corresponding elements among the view of the drawings. The headings used in the figures should not be interpreted to limit the scope of the claims.

DETAILED DESCRIPTION

Figure 1:
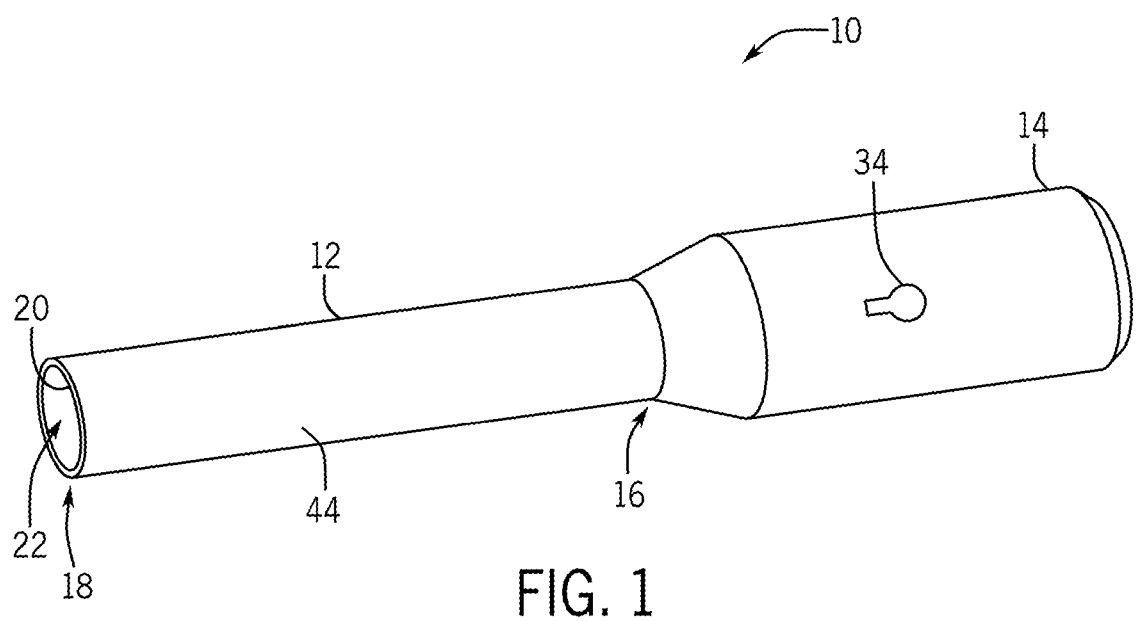
FIG. 1 illustrates a perspective view of a multipurpose medical device according to some embodiments.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

As used herein, unless otherwise specified or limited, "at least one of A, B, and C," and similar other phrases, are meant to indicate A, or B, or C, or any combination of A, B, and/or C. As such, this phrase, and similar other phrases can include single or multiple instances of A, B, and/or C, and, in the case that any of A, B, and/or C indicates a category of elements, single or multiple instances of any of the elements of the categories A, B, and/or C.

Some embodiments of the invention provide a multipurpose medical device. For example, in some embodiments, the multipurpose medical device can be configured and arranged to provide a healthcare provider, such as a surgeon or a surgical participant (i.e., a user of the device), with multiple functionalities during a medical (e.g., surgical) procedure. In particular, while some conventional surgical devices may provide one or two functions, these devices still exhibit shortcomings that are limiting to the healthcare provider and that are solved by embodiments of the invention.

By way of example only, some conventional medical devices, such as suction devices, may provide suction capabilities to the healthcare provider (e.g., to remove body fluid) and may be configured so that the healthcare provider can employ the conventional medical device to provide some measure of retraction of a tissue within the surgical field. However, use of the suction device for these unintended purposes may result in retraction overload or overexertion of force on the tissue and unexpected damage to the retracted tissue. Moreover, healthcare providers may require the use of multiple different devices for different functionalities during a procedure. As such, conventional devices may lead to the healthcare provider needing multiple and/or frequent instrument changes, which may add time and complexity to a surgical procedure. One or more embodiments of the multipurpose medical device described herein provide significant benefits to overcome the aforementioned drawbacks to these conventional devices.

For example, FIG. 1 illustrates a multipurpose medical device 10 according to some embodiments. Generally, the multipurpose medical device 10 may be used in a surgical environment, surgical training environment, or non-surgical environment by a healthcare provider (such as a surgeon) to perform one or more procedures. The multipurpose medical device 10 can provide multiple functionalities such as, but not limited to, one or more of the following: retraction, suction, stimulation, lighting, irrigation, sensing, and/or user feedback.

As shown in FIG. 1, in some embodiments, the multipurpose medical device 10 may comprise a body 12 and a handle 14. For example, at least a portion of the body 12 can be configured to contact tissue during a procedure and the handle 14 can be configured to be held by the healthcare provider to direct the body 12 in the local tissue environment during the procedure and/or control one or more functions. In some aspects, the body 12 and the handle 14 may be operatively coupled together. For example, the body 12 and the handle 14 may comprise separate elements that are coupled together using conventional coupling techniques. In some embodiments, the body 12 and the handle 14 may be reversibly coupled together such that after operative coupling, the handle 14 and the body 12 may be uncoupled from each other. In other aspects, the body 12 and the handle 14 may be substantially or completely integral with each other. In particular aspects, the body 12 and the handle 14 may be manufactured as a single unit.

In some embodiments, the body 12 and the handle 14 may comprise a material that is suitable for use in a sterile surgical environment. For example, the body 12 and/or the handle 14 may comprise a material that is capable of being sterilized (e.g., via radiation, heat, pressure, etc.) one or more times. Specifically, the body 12 and/or the handle 14 may comprise a material such as steel (e.g., stainless steel), a polymer-based material, ceramic, or any combination thereof. Additionally, the body 12 and the handle 14 may comprise the same material or different materials.

In some aspects, the body 12 and the handle 14 may be configured for a single usage, such that the materials comprising these elements need only be sterilized a single time prior to the first and only use. Moreover, in some aspects, the multipurpose medical device 10 can be suitable for usage in a non-sterile environment. For example, as described above, the multipurpose medical device 10 can be employed in a non-surgical testing environment or for demonstration purposes on a non-living specimen and, as such, the device 10 need not necessarily be sterile and/or sterilizable. However, the device 10 can still comprise materials that are capable of being sterilized for one or more non-surgical applications.

Additionally, in some embodiments, the body 12 and/or the handle 14 may comprise one or more coatings disposed thereon. By way of example only, in some aspects, the body 12 may comprise a Teflon® coating, which may reduce light reflection from the device 10 when the healthcare provider is viewing the surgical field with a microscope or otherwise.

Figure 2:
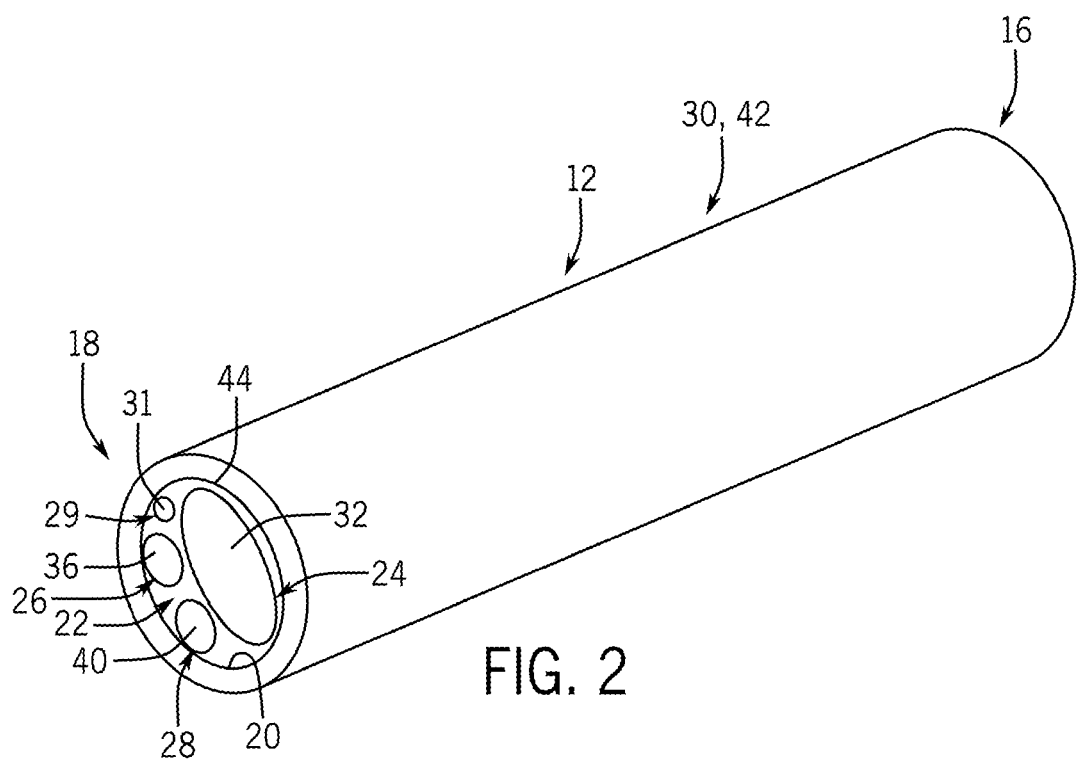
FIG. 2 illustrates a perspective view of a body of a multipurpose medical device according to some embodiments.
Figure 4A:
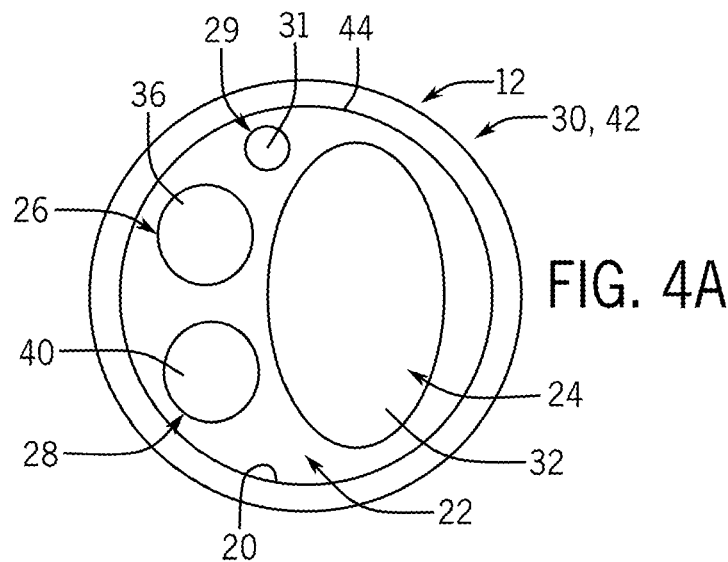
FIG. 4A illustrates a cross-sectional view of a body with a pressure-sensing film according to some embodiments.
Figure 4B:
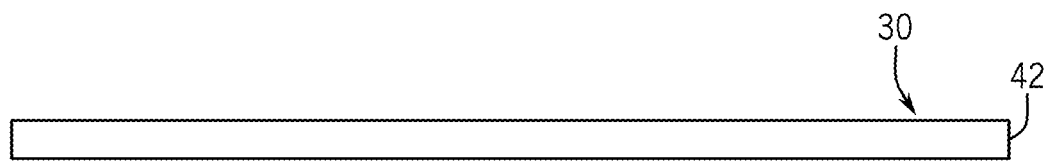
FIG. 4B illustrates a side view of the pressure-sensing film according to some embodiments.
Figure 4C:
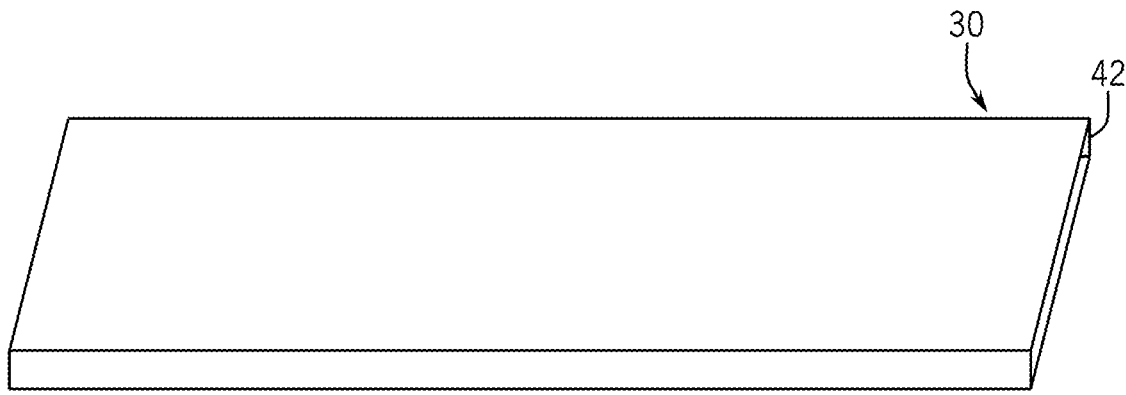
FIG. 4C illustrates an oblique view of the pressure-sensing film according to some embodiments.
Figure 7:
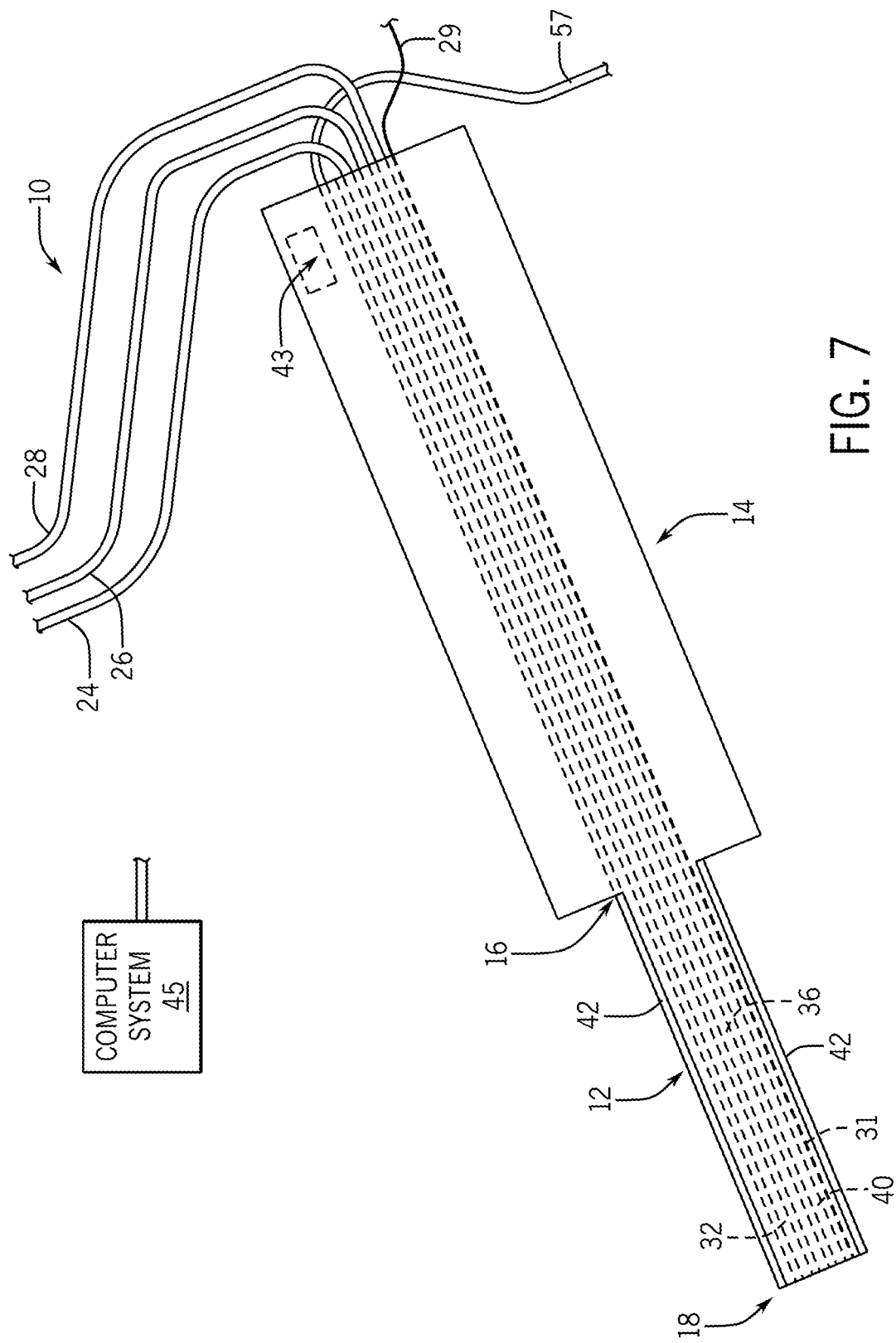
FIG. 7 illustrates a cross-sectional view of a multipurpose medical device according to some embodiments.

As illustrated in FIGS. 1, 2, and 4A, at least some aspects of the multipurpose medical device 10 may comprise a substantially circular cross-section and a generally cylindrical configuration. For example, a partial or entire length of the body 12 may comprise a circular cross-section and a substantially cylindrical configuration. Furthermore, in some aspects, one or more portions of the body 12 may comprise a non-circular cross-section, such as a square, pentagonal, hexagonal, or other shaped cross-section. Moreover, in some aspects, one or more portions of the handle 14 may comprise a similar configuration as the body 12. For example, as illustrated in FIG. 7, the handle may comprise a cylindrical configuration. In other aspects, the handle 14 may comprise a different configuration relative to the body 12. For example, as illustrated in FIG. 1, the handle may comprise an irregularly shaped configuration that is generally ergonomically configured to be comfortably held in the hand of the healthcare provider. Regardless of ergonomics, the handle 14 and the body 12 may comprise any shape, configuration, and/or cross-section desired by the healthcare providers, such as circular, cylindrical, spherical, square, pentagonal, hexagonal, and any other type of shape that is now or shall be in the future desired by healthcare providers.

In some embodiments, the body 12 may comprise a proximal end 16 and a distal end 18. For example, in some embodiments, the body 12 may comprise a substantially linear configuration such that the body 12 is generally shaped as a cylinder and the proximal and distal ends 16, 18 linearly oppose each other. In particular, in some aspects, the proximal end 16 can be the end of the body 12 that is disposed substantially adjacent to the handle 14 and the distal end 18 is at the end of the body 12 that is distal relative to the handle 14. In other embodiments (e.g., embodiments comprising a non-linear or non-cylindrical body 12), the proximal and distal ends 16, 18 can be arranged in any other manner desired by the healthcare provider and/or at least one of these elements may be omitted.

In some embodiments, the body 12 can comprise an inner surface 20. For example, in some aspects, the inner surface 20 can define a lumen 22 such that the body 12 is substantially or completely hollow. Furthermore, the lumen 22 can be configured and arranged to receive one or more multifunctional elements that may provide benefits to the multipurpose medical device 10. Moreover, in some embodiments, the lumen 22 can extend through a length of the body 12 from the proximal end 16 to the distal end 18 such that the lumen extends a length of the body 12, providing an open distal end 18 and, in some embodiments, an open proximal end 16. In some embodiments, the lumen 22 may extend for a length that is less than the full length of the body 12. In addition, in some embodiments, the body 12 and the handle 14 may be formed or coupled together such that the lumen 22 is in communication with and/or connects to a recess or lumen (not shown) within the handle 14. As such, one or more of the multifunctional elements can be positioned to extend through the body 12 and the handle 14. In other embodiments, the body 12 may comprise a plurality of lumina 22 such that one or more multifunctional elements of the multipurpose medical device 10 can be positioned in each of the lumina 22.

In some embodiments, the body 12 can comprise different size dimensions depending on the surgical procedure for which the multipurpose medical device 10 is used. For example, for a procedure such as a spine-related procedure, the body 12 may comprise an outer diameter of approximately 5 millimeters (mm) and, for a more delicate procedure (e.g., a procedure involving the brain), the outer diameter can comprise a smaller size, such as 2 mm. In other embodiments, the outer diameter may comprise a size greater than 5 mm or less than 2 mm, depending on the needs of the healthcare provider using the multipurpose medical device 10. In some embodiments, different sized bodies 12 can be interchangeable with a single handle 14 and, in other embodiments, the bodies 12 of different sizes can each have its own unique handle 14.

Similarly, an inner diameter of the body 12 (e.g., a diameter of the lumen 22) can comprise different sizes to meet the needs of the healthcare provider using the multipurpose medical device 10. For example, the inner diameter may comprise a size of 2, 3, or 4 millimeters, depending on the size of the outer diameter of the body 12 and/or the needs of the healthcare provider using the multipurpose medical device 10. Moreover, in other embodiments, the inner diameter of the body 12 can comprise a size less than 2 millimeters or greater than 4 millimeters to meet the needs of the healthcare provider using the multipurpose medical device 10. Additionally, in embodiments that comprise multiple lumina 22, the lumina 22 may be equal in diameter or may comprise different diameters to accommodate different multifunctional elements.

Figure 3A:
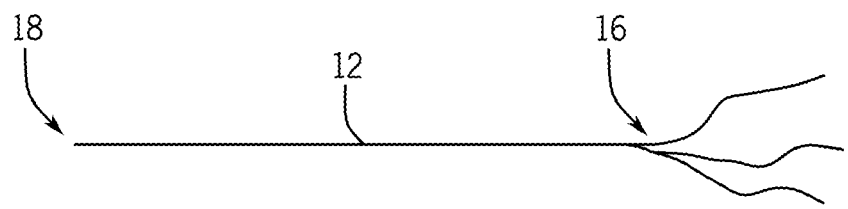
FIGS. 3A-3C illustrate side views of a body of a multipurpose medical device in different configurations according to some embodiments.
Figure 3B:
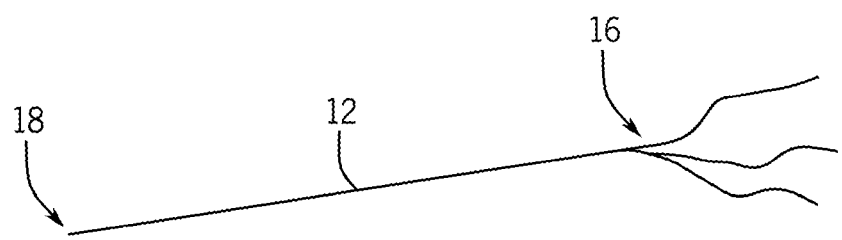
Figure 3C:
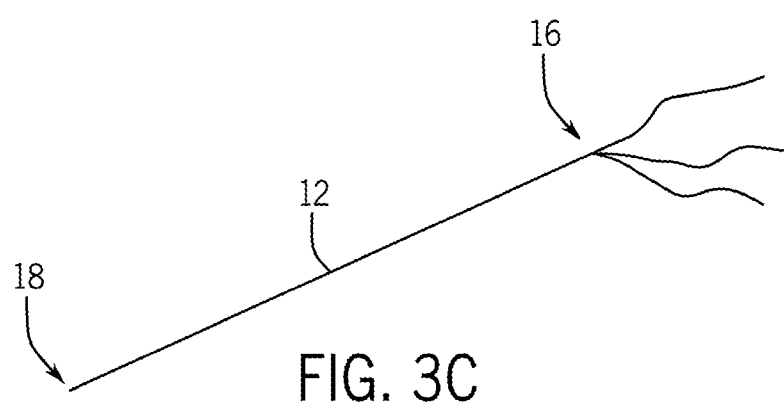

Referring now to FIGS. 3A-3C, the body 12 may comprise different configurations. For example, in some embodiments, the body 12 may comprise a substantially linear, straight configuration (as shown in FIG. 3A) such that the distal end 18 of the body 12 is substantially aligned with the remaining length of the body 12 and/or the handle 14. In other aspects, the body 12 may comprise an at least partially angled configuration (as shown in FIGS. 3B and 3C) such that the distal end 18 of the body 12 is angled with respect to at least a portion of the remaining length of the body 12 and/or the handle 14. For example, the angle can be fixed such that the body 12 can be formed so that the angle does not change during the life of the body 12. In other aspects, the body 12 can be configured and arranged so that the distal end 18 is movable with respect to at least a portion of the remainder of the body 12 and/or the handle 14. As such, the angle between the distal end 18 and the remainder of the body 12 (and/or the handle 14) can be changed from approximately 0 degrees (shown in FIG. 3A) to shallower angles (shown in FIG. 3B) to greater angles (shown in FIG. 3C), depending on the needs of the healthcare provider using the multipurpose medical device 10. Furthermore, in some embodiments, the body 12 can include a configuration having a combination of straight and angled portions.

Figure 6:
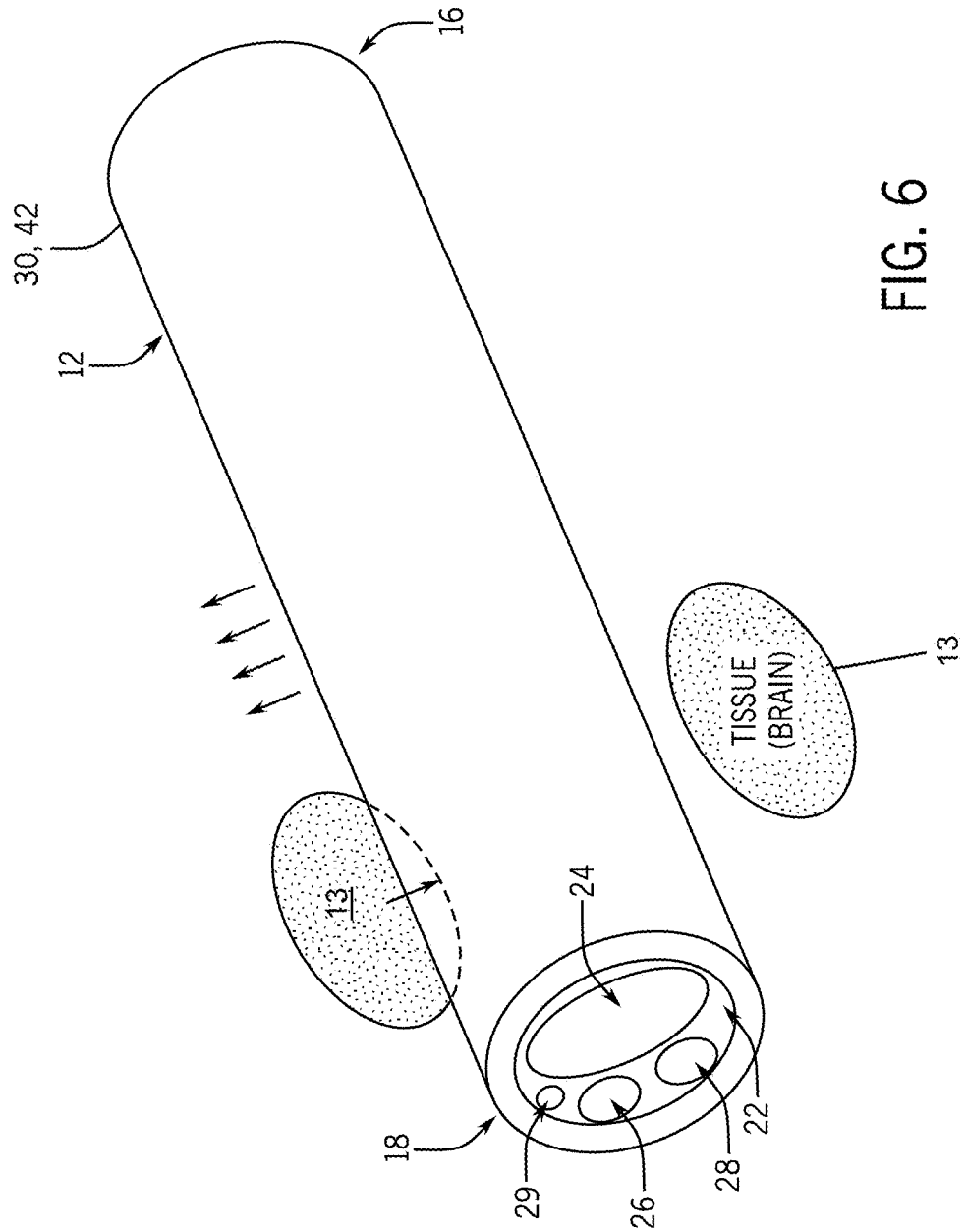
FIG. 6 illustrates retraction-based usage of a body of a multipurpose medical device according to some embodiments.

As described above, the multipurpose medical device 10 can be configured and arranged to function as an instrument to be used during one or more medical procedures. For example, the multipurpose medical device 10 can be configured and arranged to be used as a surgical retractor. In particular, the healthcare provider (e.g., a surgeon) can grasp and manipulate the multipurpose medical device 10 via the handle 14. Moreover, the healthcare provider can insert and position the multipurpose medical device 10 within the surgical field (e.g., an area of a patient where a surgical procedure is to be performed or is occurring and is kept sterile) and apply force (e.g., retracting force) to the tissues within the surgical field using the device 10 in order to retract the tissues. As such, as least a portion of the device 10, such as at least a portion of the body 12, is configured to operate as a retractor during the medical procedure. In some aspects, a surgeon can retract one or more types of tissue (e.g., brain tissue 13, as shown in FIG. 6, nerve tissue, muscle tissue, vessels, etc.) using portions of the multipurpose medical device 10 (e.g., the distal end 18 of the body 12 or other portions along the length of the body 12) to enhance visualization of normally obstructed tissues. Put another way, a surgeon could use the multipurpose medical device 10 of some embodiments as a conventional retractor as one of its functions.

The body 12 alone may be suitable for a healthcare provide to perform desired tissue retraction. However, in some embodiments, the multipurpose medical device 10 may further comprise an inflatable member (not shown). For example, the inflatable member may be generally configured as an inflatable balloon comprising medical-grade materials that can be sterilized and inflated/deflated as required by the healthcare provider using the multipurpose medical device 10. In some embodiments, the inflatable member can be supported by and/or coupled to the body 12. Furthermore, the inflatable member can be coupled to the distal end 18, or to the body 12 adjacent the distal end 18, and can be in controllable fluid communication with a fluid source (e.g., through the lumen 22 of the body 12 or other tubing). The surgeon using the multipurpose medical device 10 can activate the fluid source so that a fluid, such as air, liquid, etc., flows to the inflatable member to inflate the inflatable member to a desired pressure. As such, the inflatable member, positioned at or near the distal end 18, can provide retraction capabilities for the multipurpose medical device 10 with an atraumatic impact. Put another way, the inflatable member can be used to assist in the retraction capabilities described above. Moreover, the inflatable member can provide said retraction assistance with reduced force on the retracted tissue, which may lead to reduced surgeon-induced trauma during the medical procedure. Specifically, in some embodiments, the inflatable member can be used as the sole point of retraction force during the procedure and, in other aspects, the inflatable member can be used to augment the retraction force asserted by the surgeon using the body 12 on the tissue within the surgical field.

Referring now to FIGS. 2 and 7, the body 12 may support and/or be coupled to one or more additional functional systems of the multipurpose medical device 10. For example, the multipurpose medical device 10 may comprise a suction system 24, a stimulation system 26, an irrigation system 28, a lighting system 29, and/or a sensing system 30. It should be noted that, while the multipurpose medical device 10 shown in FIGS. 2 and 7 includes all of the functional systems, some embodiments may instead include different combinations of one or more of these functional systems.

In some aspects, the suction system 24, the stimulation system 26, the irrigation system 28, the lighting system 29, and the sensing system 30 may at be a least partially supported by the body 12. For example, in some embodiments, at least a portion of the suction system 24, the stimulation system 26, the irrigation system 28, the lighting system 29, and/or the sensing system 30 may be at least partially disposed within the lumen 22. Moreover, in some embodiments, at least some portions of the sensing system 30 may be coupled to a portion of the body 12, such as the outer surface of the body 12 and/or the handle 14. In addition, referring specifically to FIG. 7, in some aspects, some portions of the suction system 24, the stimulation system 26, the irrigation system 28, the lighting system 29, and/or the sensing system 30 may extend through some or all of the handle 14 and connect with other equipment necessary for operations and monitoring of the multifunctional medical device 10. In other embodiments, at least some of the suction system 24, the stimulation system 26, the irrigation system 28, the lighting system, and/or the sensing system 30 may be in at least partially wireless communication with other equipment necessary for operations and monitoring of the multifunctional medical device 10. Such other equipment can include, but is not limited to: a suction source, a waste receptacle, a current source, a fluid source, a power source, a lighting source, and/or a computer system 45 (shown in FIG. 7).

Referring to FIGS. 2, 4A, 5, 7, and 10, the suction system 24 can be at least partially supported the body 12 and may comprise a suction channel 32. Generally, the suction channel 32 can be positioned within the lumen 22 and extend from the distal end 18 through the proximal end 12 and, in some aspects, further extend through the handle to a suction source (not shown).

For example, the suction channel 32 can be disposed within at least a portion of the lumen 22, or depending on the embodiments, within at least one of the plurality of lumina. In some embodiments where the suction channel 32 is disposed within a portion of the lumen 22, the suction channel 32 may comprise a separate element (e.g., tubing) that may be disposed within (e.g., routed through) a portion of the lumen 22. In other embodiments, the suction channel 32 may comprise the entire lumen 22. Put another way, the suction channel 32 may comprise the lumen 22 in that the suction channel 32 is a lumen disposed within the body 12 and the handle 14. In some embodiments comprising a plurality of lumina, the suction channel 32 may be substantially or completely integral with at least one of the plurality of lumina, or may be a separate element disposed within one of the plurality of lumina. Furthermore, the suction channel 32 can be connected to a tube (e.g., adjacent the handle 14) that enables the flow of suction from the suction source (e.g., a vacuum source) to the suction channel 32.

In some embodiments, the suction source can be controlled by one or more of the healthcare providers participating in the medical procedure. For example, the suction source can be operated via an on/off switch, a foot pedal, a hand switch, or any other methodology of controlling the activation and deactivation of the suction source. Moreover, in some embodiments, the suction source may be active throughout some or all of the procedure. Furthermore, suction applied through the suction channel 32 can be selectively controlled by the surgeon. For example, in some aspects, the handle 14 may define a suction control aperture 34 (as shown in FIG. 1) that is in operative fluid communication with the suction channel 32. The suction control aperture 34 can thus be disposed through at least a portion of the handle 14 to be in fluid communication with the suction channel 32. As such, if the surgeon wishes to apply suction to a location in the surgical field, the surgeon need only obscure all or part of the suction control aperture 34 (e.g., with his or her finger, thumb, or other element) to provide suction through the suction channel 32 to remove fluid and debris from the surgical field via the distal end 18 of the body 12. Similarly, in the event that the surgeon wishes to decrease or remove all suction, the surgeon need only remove his or her finger, thumb or other element from some of all of the suction control aperture 34 to return the suction level to zero. Put another way, the suction control aperture 34 can be used to control the level of suction applied to the surgical field.

As such, the suction system 24 can be used to provide suction during the surgical procedure to remove unwanted fluids and tissue. Moreover, in combination with the retraction capabilities discussed above, the multipurpose medical device 10 can provide a combination of retraction and suction at the same or substantially the same time within the surgical field. In addition, the suction channel 32 can be in fluid communication with one or more waste receptacles (not shown). The one or more waste receptacles can be the final destination for the fluids and tissues removed from the surgical field via the suction system 24 (i.e., after flowing through the suction channel 32).

Referring now to FIGS. 2, 4A, 5, 7, and 8, the stimulation system 26 can be at least partially supported by the body 12. For example, the stimulation system 26 may comprise a stimulation channel 36 that is disposed within at least a portion of the lumen 22, or depending on the embodiments, within at least one of the plurality of lumina. For example, in some embodiments, the stimulation channel 36 may be substantially or completely integral with the lumen 22 (or at least one of the plurality of lumina). In other embodiments, the stimulation channel 36 may be disposed within a portion of the lumen 22. For example, the stimulation channel 36 may comprise a separate element (e.g., wiring) and may be disposed within a portion of the lumen 22 (or within a portion of one of the plurality of lumina).

Figure 8:
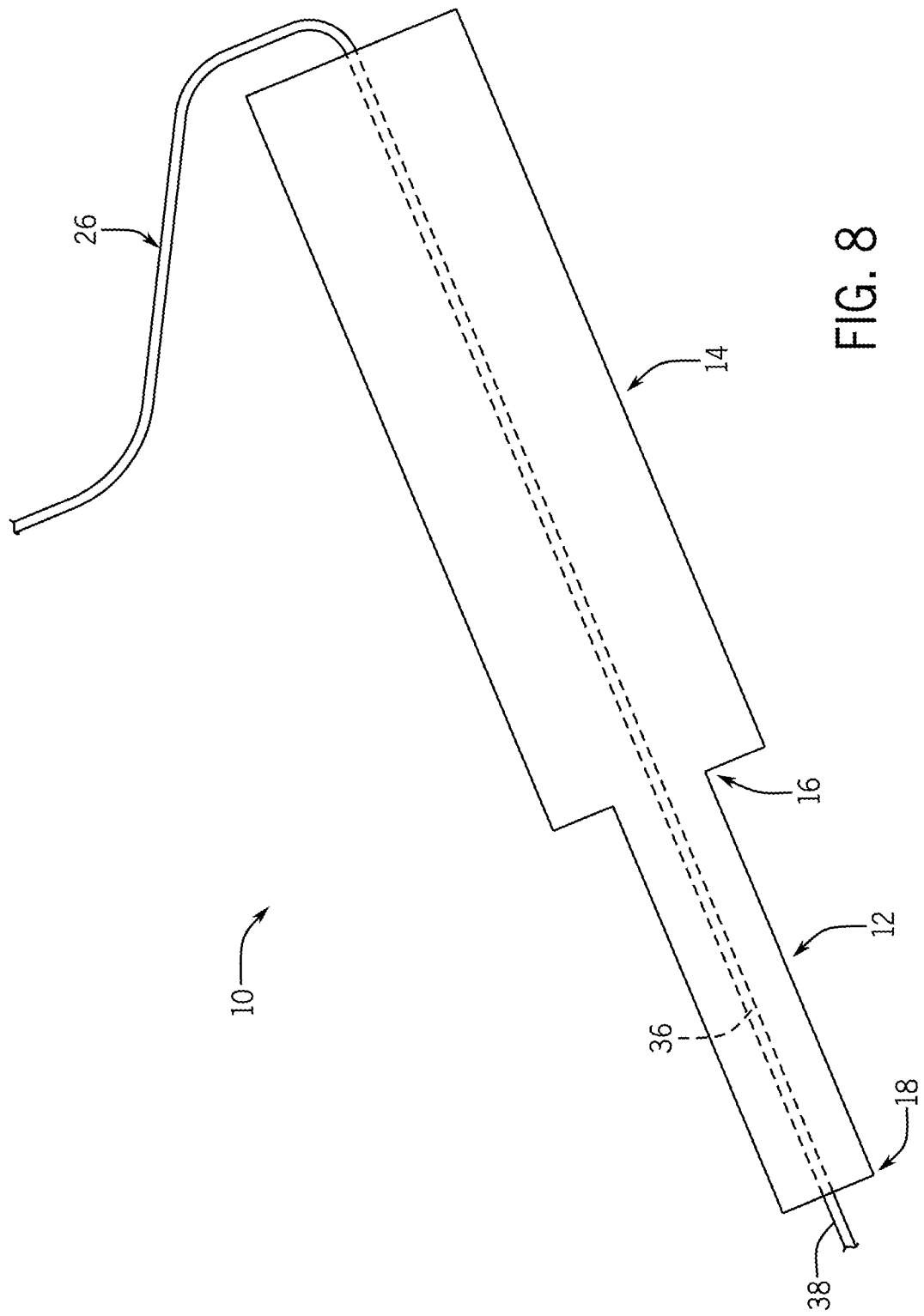
FIG. 8 illustrates a cross-sectional view of the multipurpose medical device of FIG. 7 with an isolation on a stimulation system, according to some embodiments.
Figure 9:
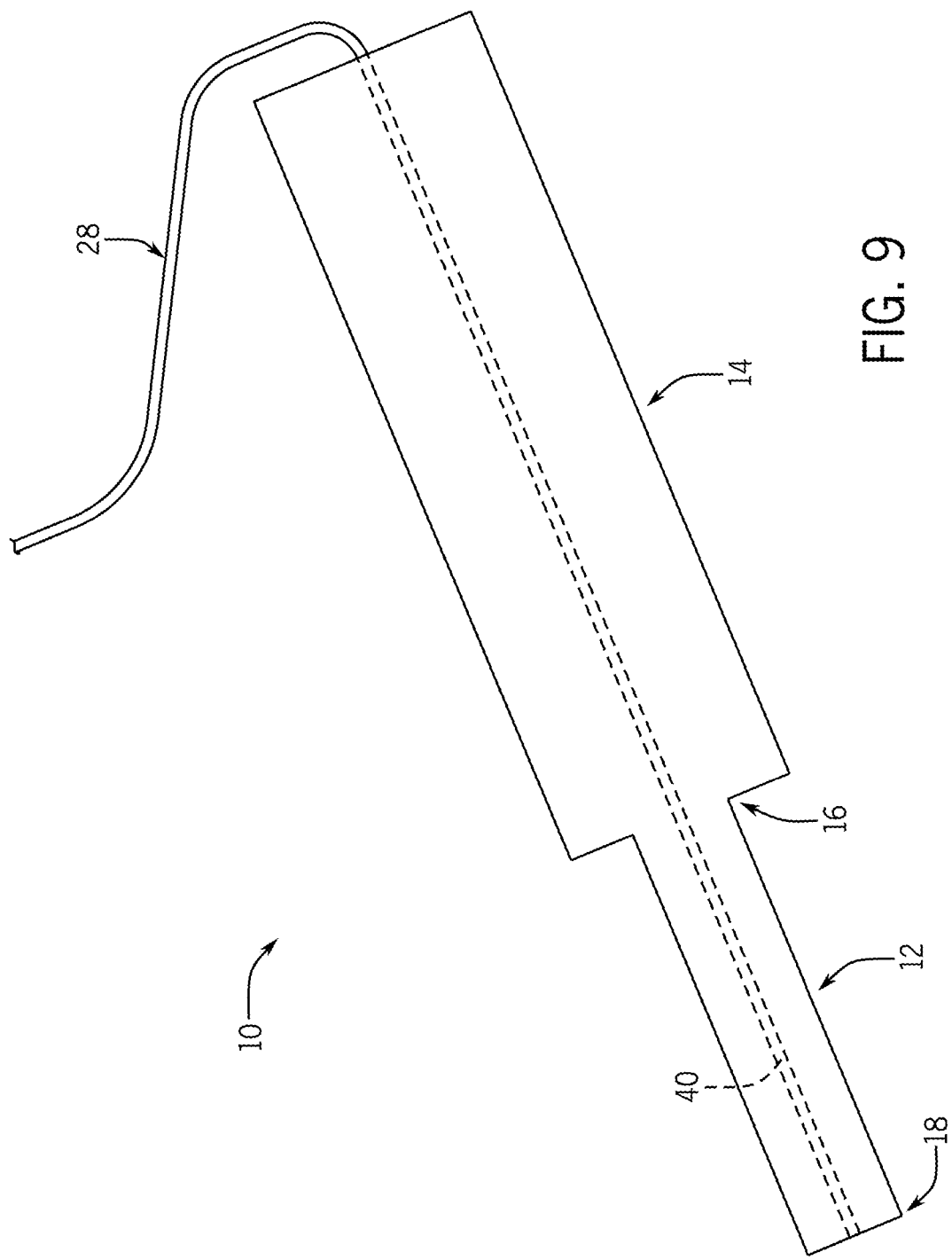
FIG. 9 illustrates a cross-sectional view of the multipurpose medical device of FIG. 7 with an isolation on an irrigation system, according to some embodiments.
Figure 10:
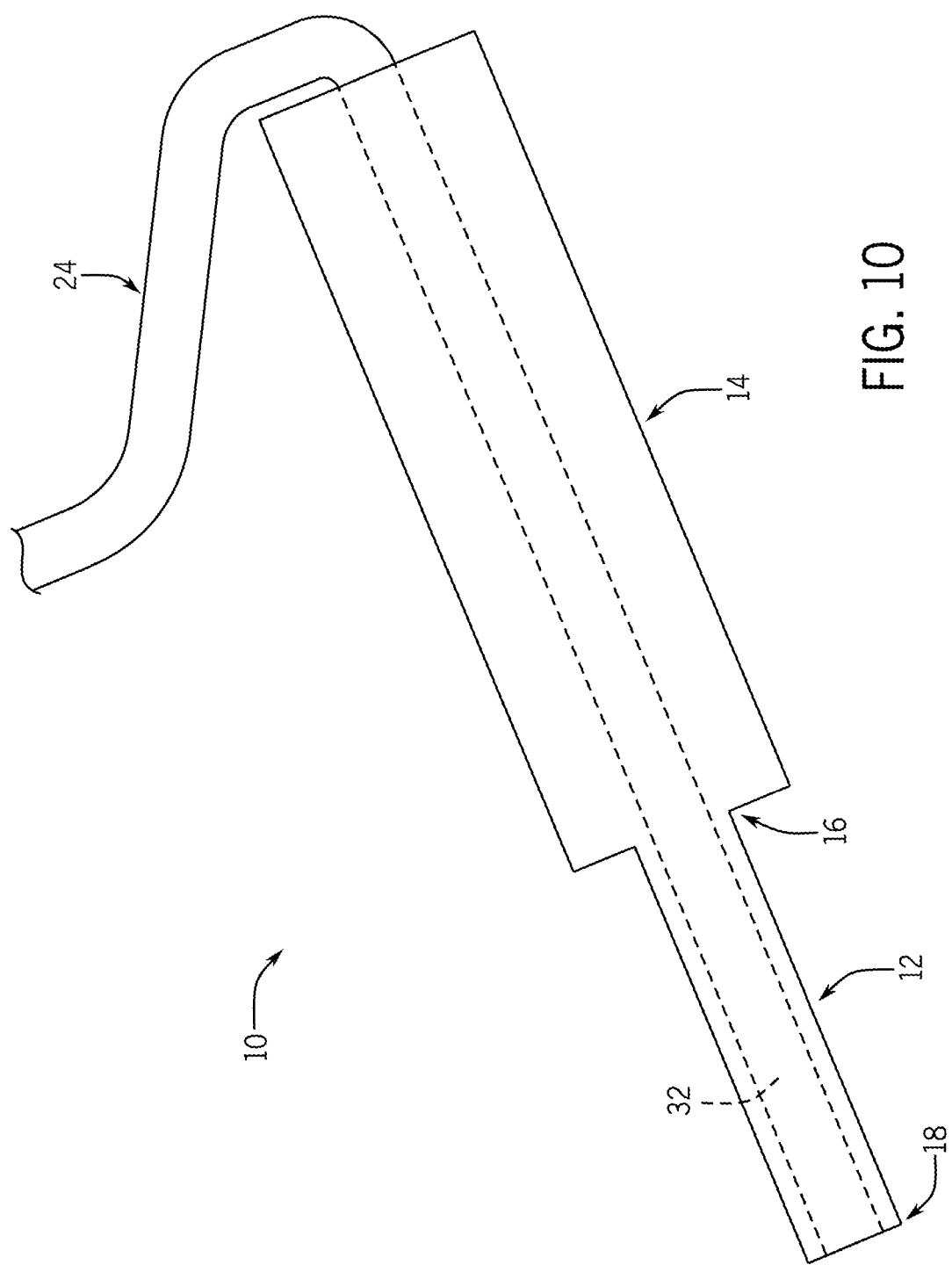
FIG. 10 illustrates a cross-sectional view of the multipurpose medical device of FIG. 7 with an isolation on a suction system, according to some embodiments.

Referring specifically to FIG. 8, in some embodiments, the stimulation system 26 generally and the stimulation channel 36, in particular, can be configured and arranged to transmit electrical current from a current source, such as a battery or other source (not shown), to a stimulator tip 38. More specifically, the stimulation channel 36 may be configured and arranged as a substantially insulated electrical wire (e.g., comprising a conductive material, such as copper) to conduct current from the current source to the stimulator tip 38. In some embodiments, operation of the stimulation system 26 can be controlled by one or more healthcare providers conducting the operation via any conventional control technology, such as an on/off switch, a foot pedal, a hand switch, etc.

In some embodiments, the stimulator tip 38 may be generally positioned at or near the distal end 18 of the body 12. For example, the stimulator tip 38 may be positioned so that when a surgeon (or other healthcare provider) desires to assess the proximity of the multipurpose medical device 10 to one or more nerves in the adjacent tissue in the surgical environment, the surgeon can activate the stimulation system 26 to conduct current from the current source to the stimulator tip 38 via the stimulation channel 36. As such, if the stimulator tip 38 is generally adjacent to one or more nerves when it provides current to the tissue, the body of the patient will accordingly respond to the electrical stimulation (e.g., via a small involuntary movement). If the surgeon determines that the device 10 is too close to one or more nerves, the surgeon can either relocate the nerves or adjust his or her location within the surgical field.

In some embodiments, the stimulator tip 38 may be configured and arranged to move depending on the activation state of the stimulation system 26. For example, in some embodiments, the stimulator tip 38 may be movable or biasable (e.g., retractable) depending on the activation state of the stimulation system 26. By way of example only, the stimulator tip 38 may be in a generally recessed position (not shown) when the stimulation system 26 is either in an inactive state or in an active state, but the surgeon does not desire to provide a current to the local tissue to assess proximity to one or more nerves. Thereafter, when the surgeon does desire to assess proximity to one or more nerves, the surgeon can release the stimulator tip 38 from the recessed position to an extend position (as shown in FIG. 8). In the extended position, the stimulator tip 83 can extend from the distal end 18 so that current can be applied to the local tissue to assess the proximity to one or more nerves. In some aspects, movement of the stimulator tip 38 can be accomplished via the use of one or more biasable members (e.g., springs) (not shown) or other retraction mechanisms.

Accordingly, the stimulation system 26 can be used to provide nerve or other stimulation during the surgical procedure. Moreover, in combination with the retraction capabilities discussed above, the multipurpose medical device 10 can provide a combination of retraction and stimulation at the same or substantially the same time within the surgical field.

Referring now to FIGS. 2, 4A, 5, 7, and 9, the irrigation system 28 can be at least partially supported by the body 12 and may comprise an irrigation channel 40. Generally, the irrigation channel 40 can be positioned within the lumen 22 and extend from the distal end 18 through the proximal end 12 and, in some aspects, further extend through the handle 14 to an irrigation source (not shown).

For example, the irrigation channel 40 can be disposed within at least a portion of the lumen 22, or depending on the embodiments, within at least one of the plurality of lumina. Moreover, in some aspects, the irrigation system 28 may be disposed in the body 12 of certain embodiments, such as those of greater outer diameter (e.g., 5 mm or greater). In other aspects, the irrigation system 28 may be configured and arranged to be disposed in a body 12 of any size or shape. In some embodiments where the irrigation channel 40 is disposed within a portion of the lumen 22, the irrigation channel 40 may comprise a separate element (e.g., tubing) that may be disposed within a portion of the lumen 22. In other embodiments, the irrigation channel 40 may comprise the entire lumen 22. Put another way, the irrigation channel 40 may comprise the lumen 22 in that the irrigation channel 40 is a lumen disposed within the body 12 and the handle 14. In some embodiments comprising a plurality of lumina, the irrigation channel 40 may be substantially or completely integral with at least one of the plurality of lumina, or may be a separate element disposed within one of the plurality of lumina. Furthermore, the irrigation channel 40 can be connected to a tube (e.g., adjacent the handle 14) that enables the flow of fluid from the fluid or irrigation source to the irrigation channel 40.

Regardless of the configuration, the irrigation channel 40 may extend through the body 12 from the proximal end 16 to the distal end 18 to enable the flow of a fluid from the fluid source, through the multipurpose medical device 10, and out the distal end 18. For example, in some embodiments, operation of the irrigation system 28 can be controlled by one or more healthcare providers conducting the operation via any conventional control technology, such as an on/off switch, foot pedal, a hand switch, etc. As such, when irrigation of at least a portion of the surgical field is desired by the healthcare provider, the irrigation system 28 can be activated to transport fluid (e.g., saline or other salt or carbohydrate-containing solution) from the fluid source through the irrigation channel 40 to the local surgical field.

Accordingly, the healthcare provider can use the irrigation system 28 to aid in clearing away (i.e., irrigating) local undesired tissue or body fluids via application of the fluid through the irrigation channel 40. Moreover, in combination with the retraction capabilities discussed above, the multipurpose medical device 10 can provide a combination of retraction and irrigation at the same or substantially the same time within the surgical field.

Referring now to FIGS. 2, 4A, 5, and 7, the lighting system 29 can be at least partially supported by the body 12. For example, the lighting system 29 may comprise a light channel 31 that is disposed within at least a portion of the lumen 22, or depending on the embodiments, within at least one of the plurality of lumina. For example, in some embodiments, the light channel 31 may be substantially or completely integral with the lumen 22 (or at least one of the plurality of lumina). In other embodiments, the light channel 31 may be disposed within a portion of the lumen 22. For example, the light channel 31 may comprise a separate element (e.g., wiring or a fiber optic cable) and may be disposed within a portion of the lumen 22 (or within a portion of one of the plurality of lumina). Furthermore, the lighting channel 31 can be connected to external wiring (e.g., adjacent the handle 14) to connect a power or light source (not shown) to the lighting channel 31.

In some embodiments, the lighting system 29 generally and the light channel 31, in particular, can be configured and arranged to emit light from the distal end 18 of the body 12. In some embodiments, operation of the lighting system 26 can be controlled by one or more healthcare providers conducting the operation via any conventional control technology, such as an on/off switch, a foot pedal, a hand switch, etc. As such, a surgeon can activate the lighting system 29 to aid in viewing the surgical field near the distal end 18.

Accordingly, the lighting system 29 can be used to provide additional lighting to the local tissue environment during the surgical procedure. Moreover, in combination with the retraction capabilities discussed above, the multipurpose medical device 10 can provide a combination of retraction and lighting at the same or substantially the same time within the surgical field.

Figure 11:
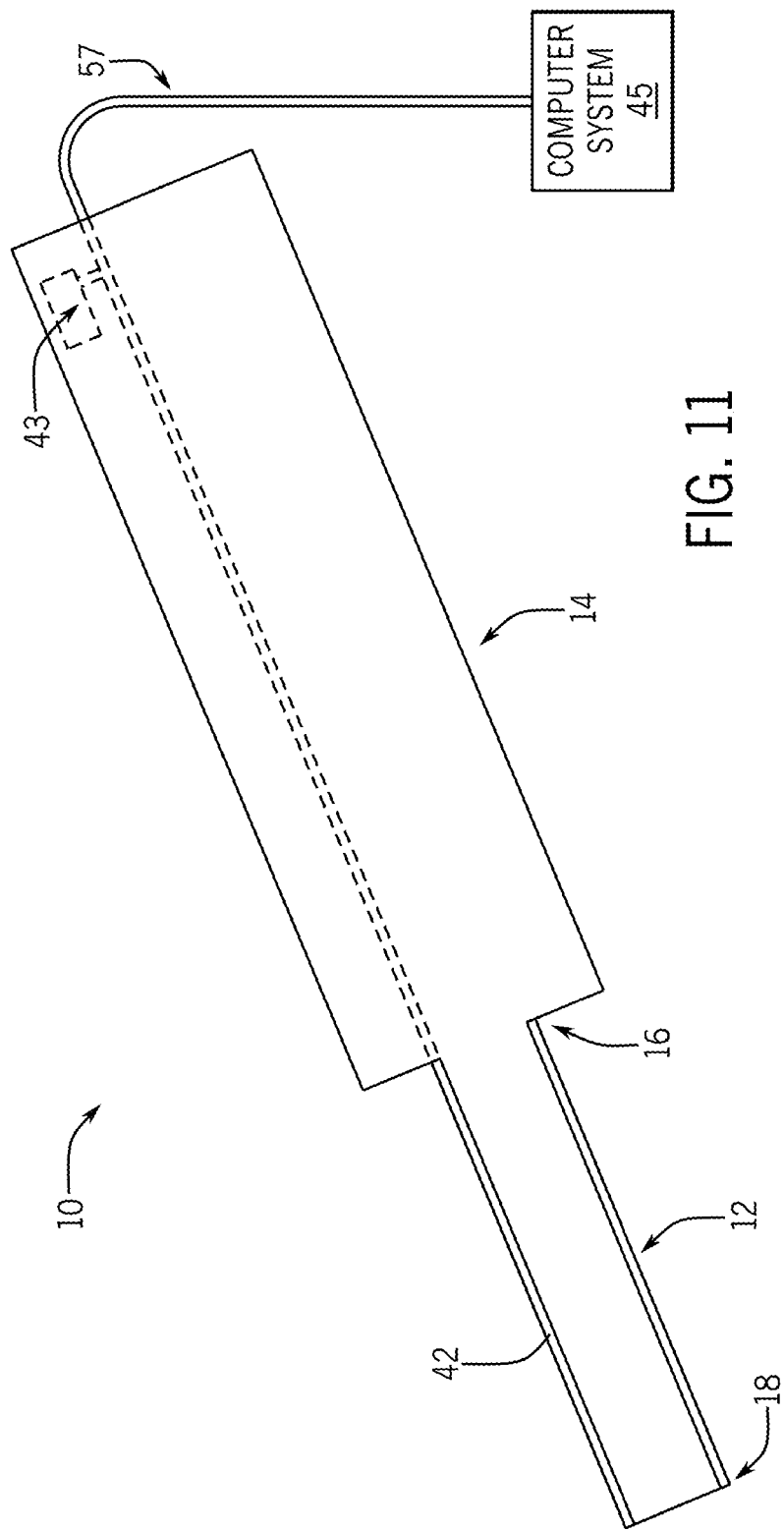
FIG. 11 illustrates a cross-sectional view of the multipurpose medical device of FIG. 7 with an isolation on a sensing system, according to some embodiments.

Referring now to FIGS. 2, 4A, 5, 6, 7, and 11, the sensing system 30 can be at least partially supported by the body 12. For example, the sensing system 30 may comprise at least one sensor 42 coupled to other otherwise disposed along the body 12 and at least one indicator 43 (as shown in FIGS. 7 and 11). In some embodiments, the sensor 42 can be configured and arranged to sense or detect an amount of force or pressure being exerted in the local environment. For example, the sensor 42 may be configured as one or more pressure sensors on the body 12 configured to detect the pressure being exerted on the local tissue by the device 10 within the surgical field. In some aspects, the sensor 42 can be used to detect a particular force or pressure (e.g., a retraction force) applied against the body 12 when the multipurpose medical device 10 is being used as a retractor to move or exert force upon one or more local tissues, such as brain tissue 13, as shown in FIG. 6. The indicator 43 can be configured to provide feedback to the surgeon (e.g., a user of the device 10) based on the sensed retraction force. More specifically, by sensing these retraction forces, force data gathered by the sensor 42 can be transmitted to the at least one indicator 43 to provide feedback to the surgeon conducting the procedure. This feedback can guide the surgeon to reduce the risk of exerting too much force on the local tissue.

Accordingly, in some embodiments, the sensor 42 can be in communication with the at least one indicator 43. For example, the sensor 42 can be in wired (e.g., see FIG. 11) or in wireless communication with the at least one indicator 43. The indicator 43 can comprise one or more of the following forms of indicators: a visual indicator (e.g., an LED that is capable of flashing or changing color), a haptic indicator (e.g., a vibrotactile signal-generating mechanism, such as a small vibrating motor), and an auditory indicator (e.g., a device that is capable of emitting one or more noises, such as a buzzer, beeping device, or other noise-generating device). Moreover, in some embodiments, the indicator 43 can be positioned on or within the body 12 or the handle 14. For example, while the indicator 43 is shown at a proximal end of the handle 14 in FIGS. 7 and 11, it may located at any position along the handle 14 or along the body 12. Furthermore, in some embodiments, the indicator 43 may be positioned in another location remote from the body 12 and the handle 14 but still proximate enough to the surgeon and surgical field to provide discernable feedback. For example, the indicator 43 can be a remote visual or auditory indicator, or a remote haptic indicator that is in contact with the surgeon, to provide feedback to the surgeon.

Additionally, in some embodiments, the indicator 43 can provide feedback if the sensed retraction force exceeds a predetermined threshold. In further embodiments, the indicator 43 can provide different feedback based on a level of retraction force sensed by the sensor 42. For example, different types of indicators 43 may signal different levels of force data acquired by the sensor 42, or a single indicator 43 may have different types of feedback based on different levels of force data. For example, a visual indicator 43 can emit different-colored light based on the force data, such as green light when the force data indicates acceptable forces up to a threshold (e.g., the above predetermined threshold) and red light when the force data indicates excessive forces above the threshold. The visual indicator 43 may alternatively include different colors than red and green, or additional colors for more levels of feedback, such as green light when the force data indicates acceptable forces up to a first threshold, yellow light when the force data indicates intermediate forces above the first threshold and up to a second threshold, where intermediate forces may still be acceptable but approaching excessive, and red light when the force data indicates excessive forces above the second threshold. In another example, different types or volumes of auditory feedback can be deployed based on the level of feedback. In yet another example, different types or level of haptic feedback (such as different types or strengths of vibration) can be deployed based on the level of feedback.

In some embodiments, the indicator 43 may be provided as part of a computer system 45 in communication with the multifunctional medical device 10 (as shown in FIG. 7). In other words, the computer system 45 may act as a remote indicator 43. For example, the multifunctional medical device 10 can be in wired or wireless communication with the computer system 45 so that force data acquired by the sensor 42 is transmitted to the computer system 45 (e.g., via wired connection 57, as shown in FIG. 7). The computer system 45 can be configured to receive the force data from the sensor 42 and can analyze the force data and provide feedback (visual, auditory, haptic, etc.) to the surgeon in real-time based on the force data (e.g., based on force measurements calculated or derived from the force data). The computer system 45 can also store the force data, e.g., for later review after a procedure or training exercise, or for other record-keeping purposes. The computer system 45 may also receive and analyze and/or store other data associated with other functions of the multifunctional medical device 10, as further described below.

Accordingly, in some embodiments, the sensing system 30 can be used to provide helpful guidance to the surgeon to avoid complications associated with over-retraction of tissues within the surgical field. While making this determination, the sensor 42 can process the amount of force, strain, or pressure sensed and provide an indication to the indicator 43 to provide feedback to the surgeon upon detection of a sensed force that exceeds a predetermined threshold. Alternatively, the sensor 42 communicates measurement data to the indicator 43 (and/or the computer system 45), which can process the amount of force, strain, or pressure sense and provide the appropriate feedback.

In some embodiments, a predetermined threshold may comprise a force detected between about 0.3 Newtons (N) to a force of about 1.5N. In some aspects, the force detected may be less than 0.3N (such as 0.1N or less) or greater than 1.5N (such as 1.84N or more). For example, for some applications, such as procedures targeting more sensitive regions of the brain, forces as low as 0.01N to 0.1N may be detected. Moreover, as noted above, the predetermined threshold may comprise multiple values such that the surgeon might receive multiple signals from the indicator 43. For example, the surgeon may receive unique feedback upon reaching predetermined thresholds of 0.3N, 0.7N, 1.0N, and 1.5N. As such, the surgeon can rely on the sensor 42 and the indicator 43 to guide the amount of force exerted when the device 10 is used as a retractor. In addition, in some aspects, the different types of indicators may signal different levels of force (e.g., auditory feedback for 1.5N, visual feedback for 1.0N, and haptic feedback for 0.3N). After receiving such feedback, the surgeon can make any changes necessary to the retractive force being applied to the local tissue within the surgical field.

Figure 5:
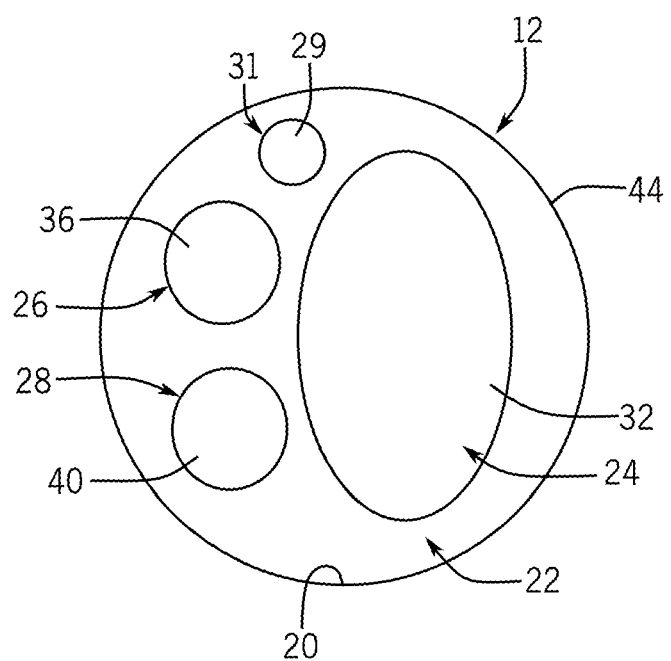
FIG. 5 illustrates a cross-sectional view of a body of a multipurpose medical device according to some embodiments.

In some aspects, the sensor 42 may be configured and arranged as a pressure-sensing device, such as a pressure-sensing film 42 that can be coupled to an outer surface 44 of the body 12 (as shown in FIGS. 2, 4A, 4B, 4C, and 6-11). In some aspects, the sensor 42 can be configured as any other technology that is capable of detecting force, strain, and/or pressure and need not necessarily be coupled to the outer surface 44 (e.g., FIG. 5 shows an embodiment operating without a sensor 42 on the outer surface 44). Further, in some aspects, at least some portions of the sensing system 30 can be disposed a distance (e.g., 5 mm) from the distal end 18 so that the sensing system 30 does not interfere with operations of the stimulation system 26 or other functional systems. In other aspects, some portions of the sensing system 30 may be positioned at the distal end 18.

In some prior devices, attempts have been made to attach a silicone retracting element, for example, to a pipe of a suction device to measure force based on displacement of water or silicone deformation. While viable due to its accuracy, disposability, and ease of sterilization, this method may not be optimal as it alters the shape of the device by imposing a size constraint that makes entering deep tissue difficult. Also, altering the physical properties of a device may modify its handling and resulting tissue interactions. This method also requires the use of cameras and other tools to ensure limited tissue damage, which litter the surgical table. As such, these prior attempts have not resulted in a viable device for medical procedures.

Some embodiments of the multifunctional medical device 10 provide an improvement over these prior methods by implementing sensors 42 as one or more strain gauges. For example, strain gauges can detect deformation (e.g., surface deformation) in response to a load (e.g., retraction or other movement of tissue in the surgical field). More specifically, a strain gauge consists of an electrical grid mounted on a backing base. By bonding the strain gauge to a surface, such as the body 12, a deformation of the surface, resulting in deformation in the strain gauge's grid, provides a strain measurement along that axis based on changes to the gauge's electrical resistance. This strain measurement is dimensionless as it is the ratio of the change in length of the surface to the original length. The direction of the strain along with its location may indicate the direction of the force and whether the surface is experiencing tension, compression, shear strain, torsion, etc.

As such, via calibration testing and calculations, one can use strain information to generally, substantially, or exactly estimate the nature and/or type of an applied load. Moreover, in some aspects, the strain information can be used to determine a relative location of the load. In some aspects, this can be viewed as an indirect manner of measuring force.

In some embodiments, the strain gauge or other sensor 42 can be supported via a fastening element, screw, or other coupling structure disposed through the body 12 or handle 14. For example, a through or blind hole can be drilled or otherwise disposed through the screw or other structure (e.g., along a central/long axis of the screw) so that the sensor 42 gauge can be disposed within and/or supported by screw.

Referring to FIGS. 12A and 12B, in some embodiments, the sensing system 30 may comprise support members 46 and strain gauges 48. For example, one or more of the support members 46 can be coupled to or otherwise supported by at least a portion of the body 12 (e.g., the outer surface 44 of the body 12). In some aspects, some or all of the support members 46 may extend some or all of the length of the body 12, as illustrated in FIG. 12A. In other embodiments, the support members 46 may comprise any other suitable length. In some aspects, the support members 46 may comprise a round, flat, regular, or irregular shape, as desired by the end user (for example, FIG. 12B illustrates a cross-sectional appearance with the support members 46 being substantially T-shaped with a flat outer surface). In some embodiments, some or all of the support members 46 may be coupled to the outer surface 44 a known distance from the distal end 18.

Moreover, in some embodiments, one or more strain gauges 48 can be coupled to the support members 46 (e.g., in a uniaxial manner). As such, as a pressure is applied to the surrounding tissue 47 by a surgeon directing the device 10 (e.g., as indicated by arrows 49 illustrated in FIG. 12A), the support members 46 may bend slightly, thereby causing the strain gauges 48 to sense tension (if the strain gauges 48 are mounted to an outer surface of the support members 46) or compression (if the strain gauges are mounted to an inner surface of the support members 46). Moreover, prior to use, the plurality of strain gauges 48 may be calibrated so that certain combinations of strain patterns will correspond to certain magnitudes of compressive force applied to the surrounding tissue. As such, the force or strain can be sensed based on the sensor readings. In some aspects, this calibration can be carried out using machine learning (e.g., via a neural network).

FIGS. 13-18 illustrate additional embodiments of a multifunctional medical device 10 including a sensing system 30 that incorporates one or more pressure sensors 42.

Figure 13:
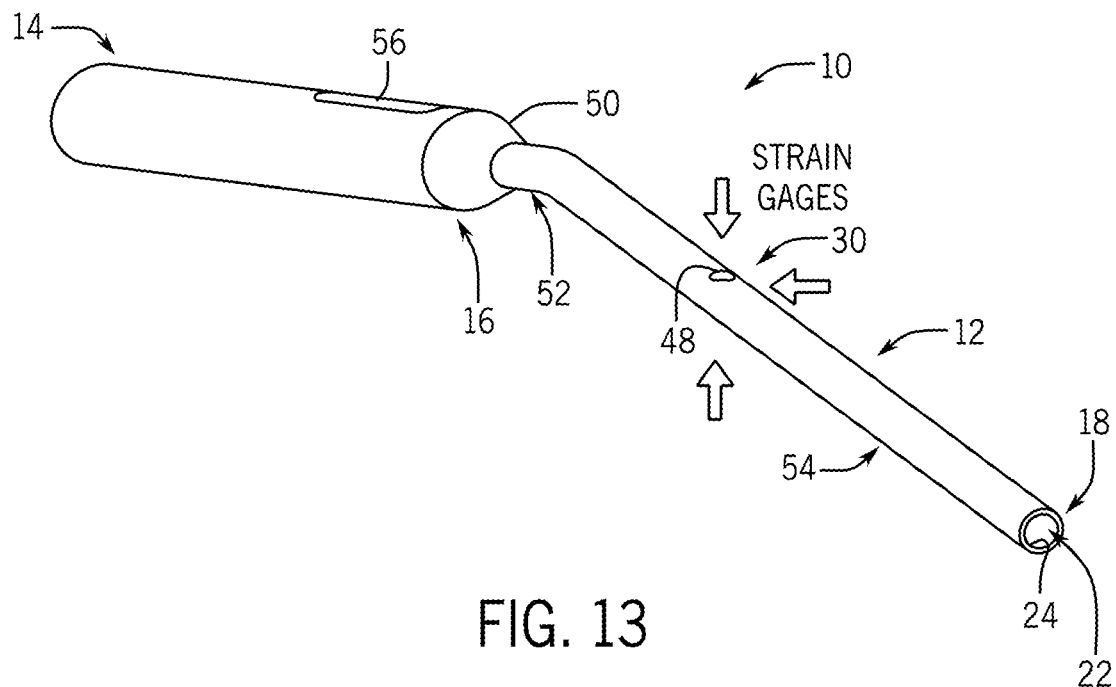
FIG. 13 illustrates a perspective view of a multifunctional medical device according to some embodiments.

For example, FIG. 13 illustrates a multifunctional medical device 10 including a sensing system 30 according to some embodiments. The multifunctional medical device 10 of FIG. 13 can include retraction, suction, and sensing functionalities. More specifically, the medical device 10 can include a body 12, a handle 14, a suction system 24, and the sensing system 30.

The body 12 and the handle 14 can include similar characteristics as that described above with respect to FIGS. 1-12A. For example, the handle 14 can be substantially cylindrical in shape and can be coupled to or integral with the body 12. The body 12 can include a proximal end 16 adjacent the handle 14, a distal end 18 distal from the handle 14, and a lumen 22 extending therethrough (e.g., acting as the suction channel 32 of the suction system 24). The body 12 can also include a tapered or rounded portion 50 at the proximal end, a straight portion 52 adjacent the proximal end 16 (e.g., aligned with the handle 14), and an angled portion 52 (e.g., angled relative to the handle 14) extending from the straight portion 52. In one embodiment, the handle 14 may comprise stainless steel 321 and the body 12 may comprise stainless steel 304 (though other materials may be contemplated in some embodiments). Additionally, in one embodiment, the body 12 can include an outer diameter that is about 4 mm. However, in some embodiments, the outer diameter of the body can range from about 2 mm to about 5 mm, as described above.

The suction system 24 can include similar characteristics as that described above with respect to FIGS. 1-12A. As such, the suction system 24 can be at least partially supported the body 12 and may comprise a suction channel 32. More specifically, the lumen 22 can act as the suction channel 32 within the body 12, and the suction channel 32 can further extend through the handle 14. From the handle 14, the suction channel 32 can be connected to tubing that is further connected to a suction source. The handle 14 can also include a suction control aperture 56 in communication with the suction channel 32, permitting the healthcare provider to selectively control suction from the distal end 18, as described above.

Accordingly, the multifunctional medical device 10 of FIG. 13 can provide three functions: suction, retraction, and sensing/feedback. Furthermore, though not shown in FIG. 13, in some embodiments, the multifunctional medical device 10 can also include additional functional systems, such as a stimulation system, an irrigation system, and/or a lighting system.

With respect to the sensing system 30, the multifunctional medical device 10 can include one or more sensors and, more specifically, one or more strain gauges 48 coupled to an outer surface 44 of the body 12. Bonding the strain gauges 48 to the outer surface 44 imposes minimal, if any, size constraints on the device 10 due to the thin grid of the strain gauge 48. Additionally, in some embodiments, a coating and/or adhesive can be applied over the strain gauges 48 to enable sterilization of the multifunctional medical device 10 without affecting strain gauge function.

Figure 14:
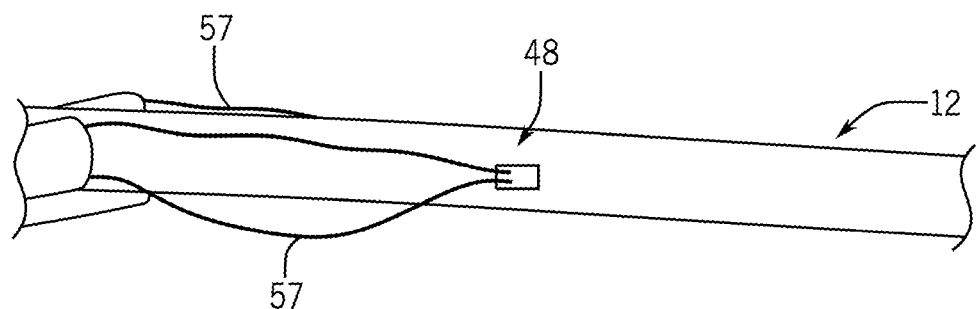
FIG. 14 illustrates a partial perspective view of the multifunctional medical device of FIG. 13.

For example, as shown in FIG. 13, three strain gauges 48 can be positioned around a circumference of the body 12 (e.g., of the angled portion 54 of the body 12), at about 90-degree increments. However, in some embodiments, more or fewer strain gauges 48 may be used, e.g., as limited by the circumference of the body 12. Furthermore, as shown in FIG. 13, the strain gauges 48 can be positioned a distance away from the distal end 18. In one embodiment, the strain gauges 48 can be positioned about 6.8 cm from the distal end 18 (though other lengths may be contemplated in other embodiments). Additionally, in some embodiments, as shown in FIG. 14, the strain gauges 48 can include external wired connections 57, for example, that can be connected to a computer system 45 or other data acquisition system. In other embodiments, the strain gauges 48 can be coupled to internal wiring (not shown) routed through the lumen 22 and the handle 14.

In some embodiments, the strain gauges 48 can include uniaxial strain gauges (that is, capable of measuring strain in a single direction) or rosette gauges (that is, two, three, or more gauges positioned at incremental angles relative to one another, capable of measuring strain in two, three, or more directions, respectively). The rosette gauges according to some embodiments may be spaced apart or stacked. Notably, stacked rosette gauges can require less surface area than spaced-apart rosette gauges and include all grids stacked over a single point, allowing measurements from all grids to be the same plane. Accordingly, the multifunctional medical device 10 of some embodiments can include any number and type of gauge configurations.

For example, the strain gauges 48 illustrated in FIG. 13 can be uniaxial strain gauges or rosette gauges and can be oriented to detect bending forces of the body 12. More specifically, uniaxial strain gauges 48 can be oriented longitudinally along the body 12 (e.g., along a longitudinal axis of the body 12) and/or rosette strain gauges 48 can include one gauge that is oriented longitudinally along the body 12. As a result, the strain gauges 48 can sense bending forces of the body 12. That is, when a force is applied to the body 12, such as when a point adjacent the distal end 18 presses against tissue to retract the tissue, the body 12 will slightly deform and one or more of the strain gauges 18 can sense this bending strain. Furthermore, the strain gauges 48 are able to sense these forces despite being applied to the curved surface of the body 12 (i.e., rather than a traditional flat surface).

Figure 15:
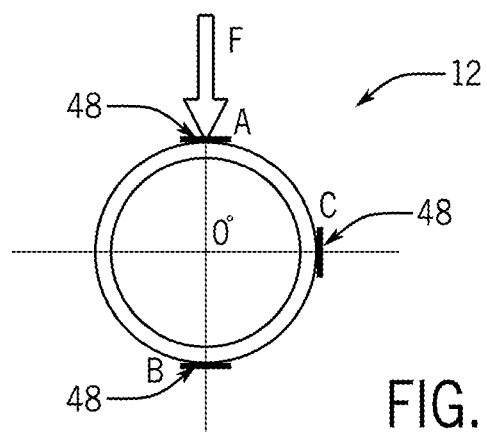
FIG. 15 illustrates a schematic cross-sectional view of the multifunctional medical device of FIG. 13 with a force being applied to the multifunctional medical device.

By way of example, if a force F is applied to the body 12 as shown in FIG. 15, the body 12 will deform downward (relative to the orientation illustrated in FIG. 15), so that a top surface of the body 12 expands and the gauge 48A will sense this tension, and a bottom surface of the body 12 compresses and the gauge 48B will sense this compression. The other gauge 48C will generally not sense a bending force, or have minimal response to bending in the direction shown in FIG. 15, because bending strain is zero at the geometric centroid of a cross-sectional shape. More specifically, because the lumen of the body 12 is symmetrical and circular in cross-section, the geometric centroid would be along a horizontal line extending through the circle's center. The other gauge 48C lies along this line of no stress/strain, referred to as the neutral axis. Furthermore, if the force F is applied at a point between two strain gauges 48, then all three strain gauges 48 can sense some component of the force application. The computer system 45 can combine the measurements from the strain gauges 48 around the body 12 to determine the total force applied. For example, the multifunctional medical device 10 can be calibrated to determine a relationship between strain measurements and different angles of perpendicular force application. Using these relationships as a calibration measure, unknown forces and angles of application can be predicted. Thus, by using multiple strain gauges 48 disposed around the circumference of the body 12, forces applied against any location around the body 12 can be detected and calculated.

Furthermore, any change in strain measurements caused by fluid flow through the lumen 22 (such as suction at conventional vacuum pressures for medical procedures), can be accounted for by the computer system 45 and filtered out from the final force determinations. For example, a study was conducted showing that starting and stopping of fluid flow may cause a bias in strain readings that can be accounted for, though changes in pressure of the flow once it started or stopped was shown to have minimal effect on strain measurements. As such, in some embodiments, the computer system 45 can also receive inputs regarding operation of the irrigation system 28.

Accordingly, by measuring bending strain around a circumference of the body 12, force measurements can be obtained. However, to determine actual force measurements based on bending strain, a moment arm must be known. That is, a distance of force application from the strain gauges 48 must be known. Thus, if a multifunctional medical device 10 is configured so that force application is only applied at a known distance from the strain gauges (e.g., along the first two centimeters from the distal end 18), bending strain can be used to obtain force measurements. On the other hand, if the multifunctional medical device 10 is configured so that force application may be applied at any distance along a length of the body 12, bending forces alone may be insufficient to accurately calculate force. More specifically, the dependence on the moment arm may make it difficult to solve for force as the area of contact is not known. As such, additional strain measurements may be necessary in some embodiments.

For example, in addition to measuring bending strain, rosette gauges can measure shear strain (i.e., due to having multiple gauges in multiple directions), which is independent of the location of applied force. More specifically, stacked rosette gauges, such as 3-gauge rosettes, positioned circumferentially around the body 12 can provide measurements in three directions, provide a more comprehensive measure of strain circumferentially (as compared to uniaxial gauges alone), and provide the ability to compute shear strain as well as bending strain to compare calibrations using both parameters. For example, shear strain can be computed using established strain theory principles and the three uniaxial strains from each gauge in the stack of a rosette strain gauge 48. Additionally, shear and bend strain together can be used to calibrate the multifunctional medical device 10 so that unknown forces and angles of application, as well as unknown distances from the gauges 48, can be predicted. Furthermore, in some embodiments, the rosette gauges can further be used to determine maximum and minimum principle strain along with the angle at which these principle strains lie.

Figure 16A:
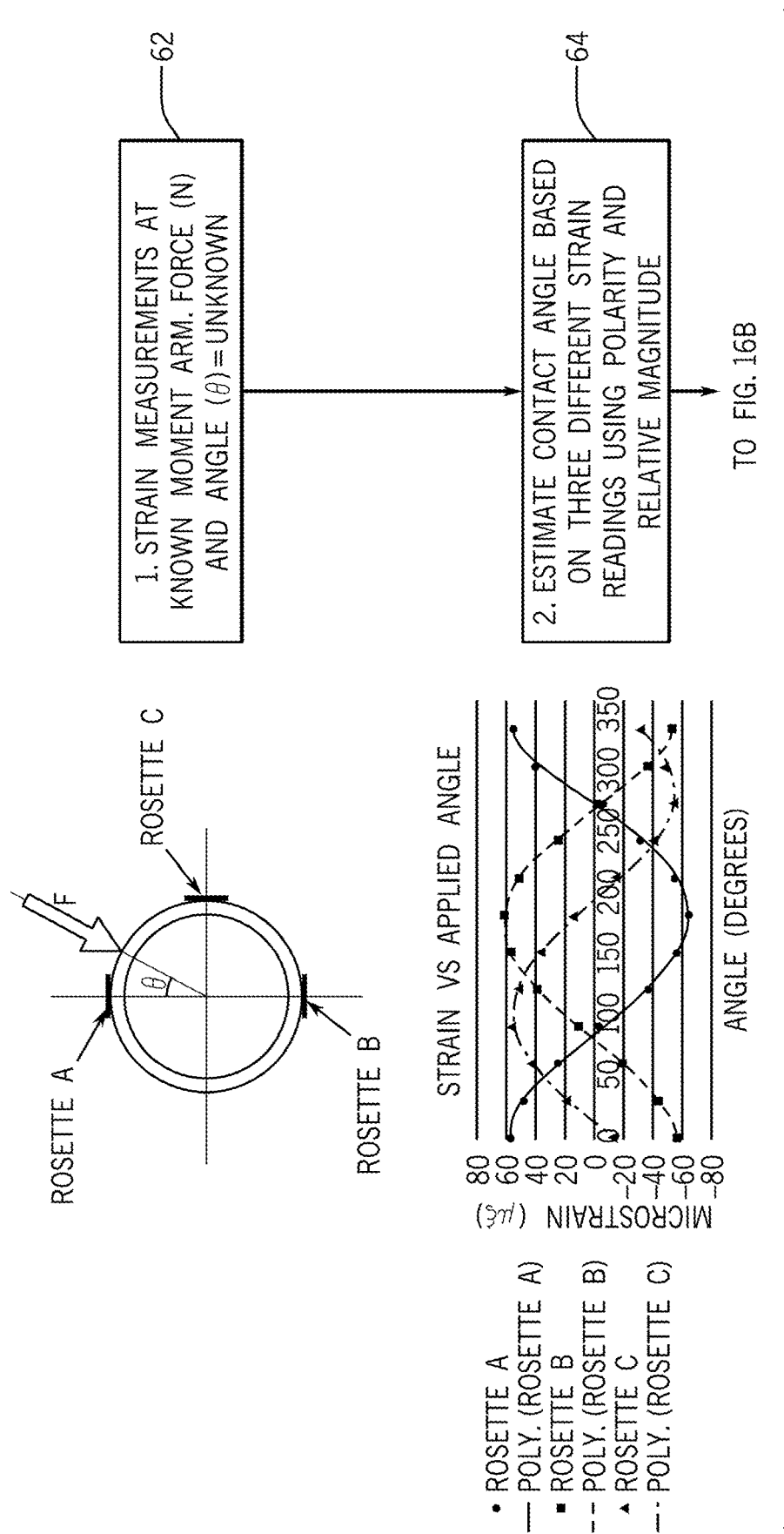
FIGS. 16A and 16B illustrates a flow chart of a method for determining a force applied to the multipurpose medical device of FIG. 13.
Figure 16B:
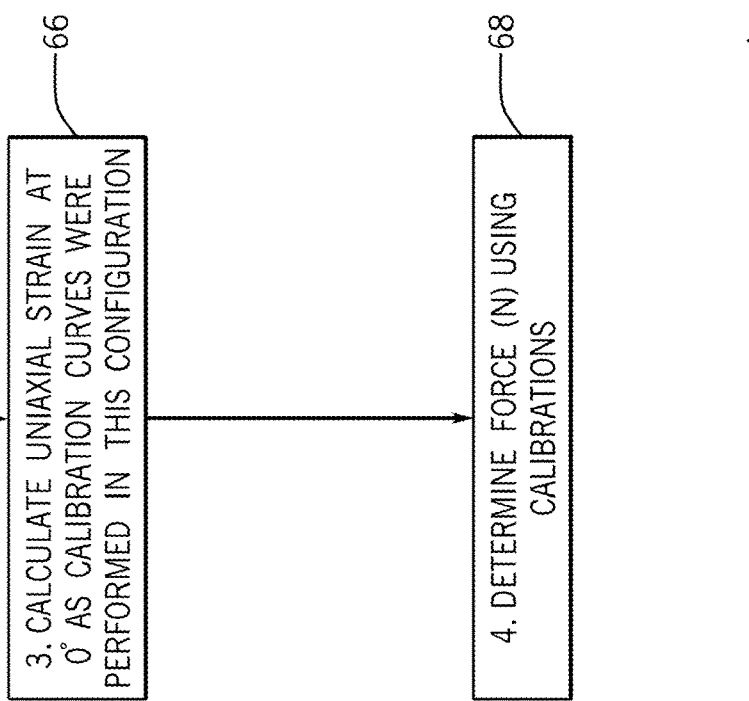
Figure 16B:
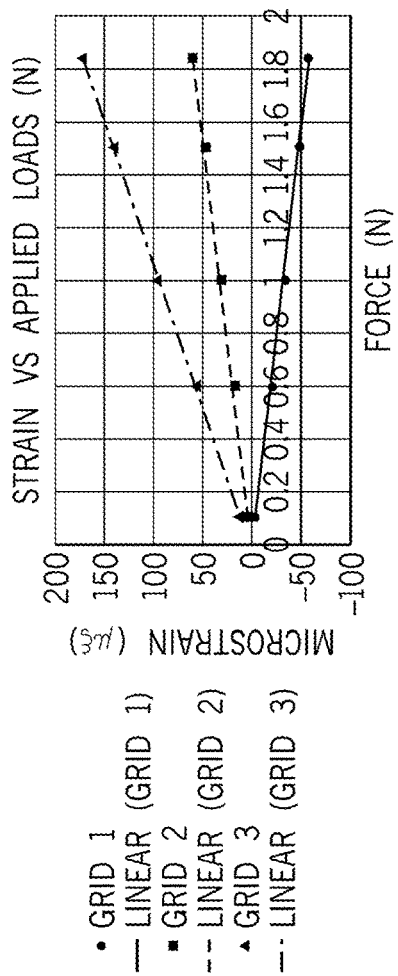

By way of example, FIGS. 16A and 16B illustrates one method of calculating force and contact angle using calibrations established from a circumferential rosette gauge 48 and incremental angle experiments when the moment arm is known. Each circumferential rosette gauge 48 is positioned so that one of its three uniaxial gauges is positioned along the long axis of the lumen (i.e., the body 12) or, alternatively, uniaxial gauges alone may be used with this method. Given strain measurements from the grids facing the length of the body 12 from each rosette gauge 48 (or each uniaxial gauge), based on an applied force having a known moment arm (step 62), an angle may be approximated using polarity and relative magnitude of the three strain readings (step 64). Strain vs. angle calibrations exhibit a sinusoidal trend, as shown in FIG. 16A. As such, angle can be estimated using a polarity of each reading (e.g., to find a region that includes all curves in the correct polarity), and relative magnitudes (e.g., if one reading is greater than the other, then the initial region can be narrowed to a smaller region where gauge's curve should be above the other gauge's curve), and points of magnitude intersection and equivalency (e.g., if two measurements are close in magnitude and not near the x-axis, the smaller region can be narrowed further to a point where those curves intersect away from the x-axis). Using this methodology, the curves can be used as a guide to estimate angle within ±25°, in some embodiments. The strain measurements are then divided by the cosine of the approximated angle to solve for uniaxial strain, that is, strain at 0° (step 66). Linear rosette calibrations (performed when the force was applied at that angle) can then be applied to the normalized strain measurements. More specifically, force can be determined using the linear calibrations, based on the given moment arm, for the individual rosettes and their grids (step 68).

Accordingly, in some embodiments, the multifunctional medical device 10 of FIG. 15 can include rosette gauges 48 around the circumference of the body 12 and be configured to measure strain as well as bending forces. In some embodiments, however, the circumference of the body 12 may be so small that the rosette gauges 48 wrap too far around the body 12, causing shear strain measurements that are not independent (e.g., measurement that include loads other than shear). Thus, in some embodiments, as shown in FIG. 17, a multifunctional medical device 10 can include a sensing system 30 and a modified body geometry that accounts for this impediment to independent shear strain measurement.

Figure 17:
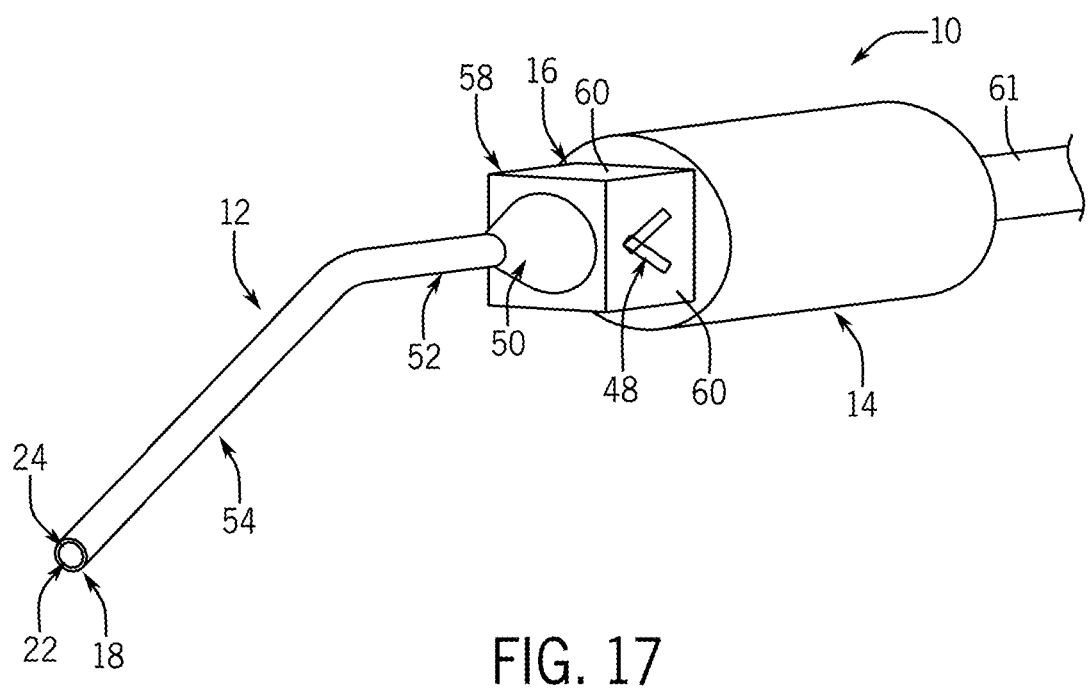
FIG. 17 illustrates a perspective view of a multifunctional medical device according to some embodiments.

More specifically, multifunctional medical device 10 of FIG. 17 can include a body 12, a handle 14, a suction system 24, and the sensing system 30. The multifunctional medical device 10 can thus include retraction, suction, and sensing functionalities. Here, the suction system 24 can include similar characteristics as that described above with respect to FIGS. 1-15. For example, FIG. 17 illustrates a suction tube 61 coupled to the handle 14 (e.g., in communication with a suction channel 32 extending through the handle 14 and the body 12). Furthermore, though not shown in FIG. 17, in some embodiments, the multifunctional medical device 10 can also include additional functional systems, such as a stimulation system, an irrigation system, and/or a lighting system.

According to some embodiments, the body 12 and the handle 14 can generally include similar characteristics as that described above with respect to FIGS. 1-15. For example, the handle 14 can be substantially cylindrical in shape. The body 12 can include a proximal end 16 adjacent the handle 14, a distal end 18 distal from the handle 14, and a lumen 22 extending therethrough (e.g., acting as the suction channel 32 of the suction system 24). In one embodiment, the handle 14 may comprise stainless steel 321 and the body 12 may comprise stainless steel 304 (though other materials may be contemplated in some embodiments). Additionally, in one embodiment, the body 12 can include an outer diameter that is about 4 mm. However, in some embodiments, the outer diameter of the body can range from about 2 mm to about 5 mm, as described above.

The body 12 can also include a tapered or rounded portion 50 adjacent the proximal end, a straight portion 52 adjacent the tapered portion 50 (e.g., aligned with the handle 14), and an angled portion 52 (e.g., angled relative to the handle 14) extending from the straight portion 52. The body 12 can further include an intermediate portion 58, for example, at or near the proximal end 16 adjacent the handle 14 (or at another location along the length of the body 12). As shown in FIG. 17, the intermediate portion 58 including one or more flat faces 60. For example, the intermediate portion 58 can include a cross-section that is square, pentagonal, hexagonal, heptagonal, octagonal, or other shapes having one or more flat surfaces.

With respect to the sensing system 30 of FIG. 17, the multifunctional medical device 10 can include one or more sensors and, more specifically, one or more strain gauges 48 coupled to the flat surfaces 60 of the intermediate portion 58. By way of example, FIG. 17 illustrates one strain gauge 48 (e.g., a two- or three-axis rosette gauge) bonded to one of the flat surface 60, though additional strain gauges 48 can be bonded to each of the flat surfaces 60 (or less than all of the flat surfaces 60). For example, in one embodiment, the multifunctional medical device 10 includes four strain gauges 48 each mounted on a respective flat surface 60. In another embodiment, the multifunctional medical device 10 includes eight strain gauges 48 each mounted on a respective flat surface 60. In some embodiments, the strain gauges 48 can include external wired connections (not shown), for example, that can be connected to a computer system 45 or other data acquisition system. In other embodiments, the strain gauges 48 can be coupled to internal wiring (not shown) routed through the lumen 22 and the handle 14.

By being applied to a flat surface 60, each strain gauge 48 can enable more accurate, independent shear strain measurements. As described above, shear load measurements can be used to determine applied force independent of the moment arm (i.e., independent of the location of applied force). Thus, the computer system 45 can calculate force applied by the multifunctional medical device 10 against a tissue based on measurements from the strain gauges 48 and provide feedback to the surgeon operating the device 10 (either through the computer system 45 or a separately connected indicator 43) based on the calculated force.

As described above, the device 10 can include strain gauges 48 to obtain shear strain measurements. In some embodiments, different device designs and strain gauge 48 positioning can cause the device 10 (or portions thereof) to act similar to a shear beam load cell. In a first example, the strain gauges 48 are positioned directly on the body 12 and oriented to maximally sense shear strain, as described above. In another example, the body 12 may include one or more recessed portions (not shown). Each recessed portion (e.g., machined into the body 12) can form a shear web, where strain gauges 48, such as two-axis rosette gauges, are positioned on either side of the shear web to produce an output proportional to the shear force applied against the body 12 (e.g., in one component direction). In some aspects, the opposing strain gauges can be connected in a full-bridge circuit to render the output insensitive to off-axis load components or side loads.

Furthermore, in some embodiments, the device 10 may include additional structures with strain gauges 48 to sense shear strain. In one example, the strain gauges 48 are positioned along flat surfaces 60 of the intermediate portion 58, as described above. In another example, the body 12 or the intermediate portion 58 can include one or more elastic beam elements (not shown), such as two or three elastic beam elements in parallel (e.g., forming a parallelogram elastic element connected by rigid flanges). Uniaxial tension/compression strain gauges 48 can then be coupled to one or more of the beam elements to sense applied shear forces (e.g., a gauge 48 near the applied force would sense compression, while a gauge 48 further from the force would sense tension). In yet another example, several small orthogonal parallelogram or shear beam elements can be assembled in series, each with a different directional sense, and including attached strain gauges 48. In one aspect, the intermediate section 58 can comprise two orthogonal parallelogram elements to measure both vertical and horizontal force components. In this aspect, the body 12 can continue through the intermediate section 58 (e.g., as flexible tubing) to the handle 14, but would transfer load to the intermediate section 58 rather than the handle 14. Thus, the handle 12 and the body 12 would be coupled structurally via the intermediate section 58, which would generally act as a "spring" element to detect force. It should be noted that additional designs not specifically described herein may be contemplated within the scope of this disclosure to generally provide a device 10 including one or more strain gauges 48 coupled to the body 12 and/or to one or more additional structures to determine shear loads.

Figure 18:
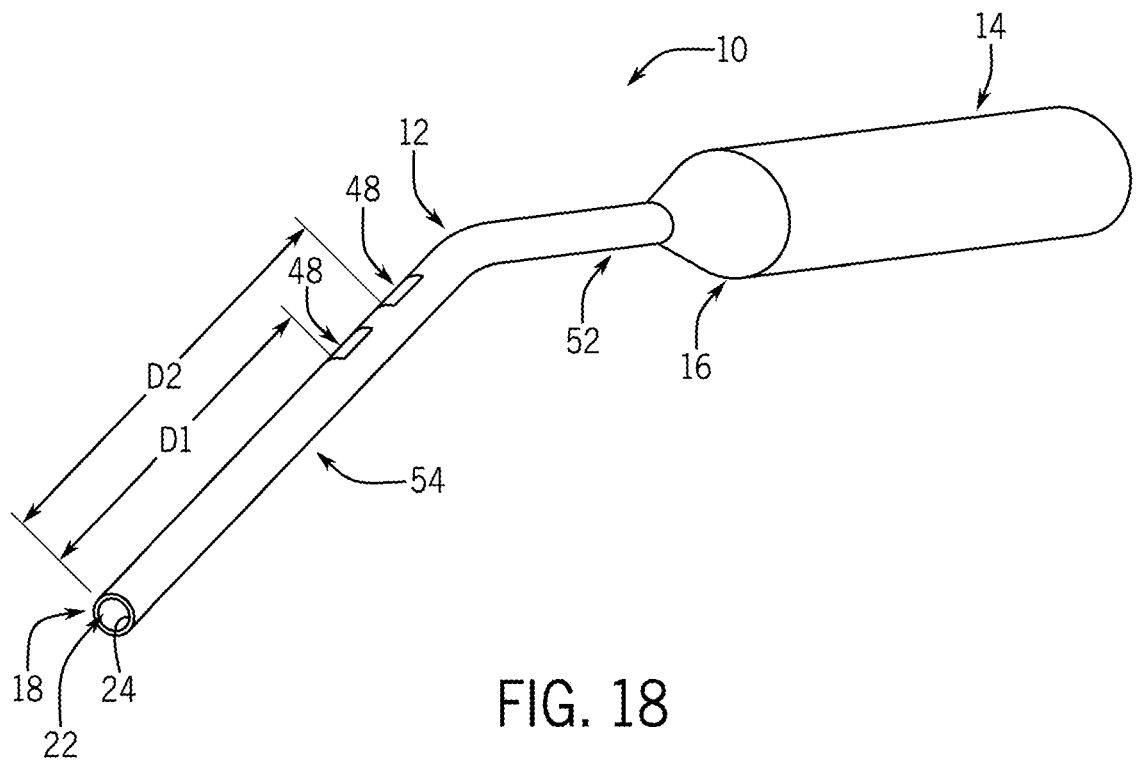
FIG. 18 illustrates a perspective view of a multifunctional medical device according to some embodiments.

Additionally, FIG. 18 illustrates a multifunctional medical device 10, according to some embodiments, that can include a sensing system 30 configured permit force measurement and calculation without prior knowledge of the point of force application.

More specifically, multifunctional medical device 10 of FIG. 18 can include a body 12, a handle 14, a suction system 24, and the sensing system 30. The multifunctional medical device 10 can thus include retraction, suction, and sensing functionalities. Here, the suction system 24 can include similar characteristics as that described above with respect to FIGS. 1-15 and 17. Furthermore, though not shown in FIG. 18, in some embodiments, the multifunctional medical device 10 can also include additional functional systems, such as a stimulation system, an irrigation system, and/or a lighting system.

According to some embodiments, the body 12 and the handle 14 can generally include similar characteristics as that described above with respect to FIGS. 1-15. For example, the handle 14 can be substantially cylindrical in shape. The body 12 can include a proximal end 16 adjacent the handle 14, a distal end 18 distal from the handle 14, and a lumen 22 extending therethrough (e.g., acting as the suction channel 32 of the suction system 24). The body 12 can also include a straight portion 52 adjacent the proximal end 16 (e.g., aligned with the handle 14) and an angled portion 54 (e.g., angled relative to the handle 14) extending from the straight portion 52 (and, optionally, a tapered or rounded portion 50 adjacent the proximal end 16). In one embodiment, the handle 14 may comprise stainless steel 321 and the body 12 may comprise stainless steel 304 (though other materials may be contemplated in some embodiments). Additionally, in one embodiment, the body 12 can include an outer diameter that is about 4 mm. However, in some embodiments, the outer diameter of the body can range from about 2 mm to about 5 mm, as described above.

With respect to the sensing system 30 of FIG. 18, the multifunctional medical device 10 can include two or more in-line sensors and, more specifically, two or more in-line strain gauges 48 coupled to the body 12 (e.g., to the angled portion 54) and positioned at different distances from the distal tip 18. By way of example, FIG. 18 illustrates a first strain gauge 48 (e.g., a uniaxial or a two- or three-axis rosette gauge) bonded to the body 12 at a first distance D1 from the distal end 18, and a second strain gauge 48 (e.g., a uniaxial or a two- or three-axis rosette gauge) bonded to the body 12 along the same axis as the first strain gauge 48, but at a second, further distance D2 from the distal end 18. In some embodiments, the multifunctional medical device 10 includes these in-line pairs of strain gauges 48 positioned around a circumference of the body 12. Additionally, in some embodiments, the strain gauges 48 can include external wired connections (not shown), for example, that can be connected to a computer system 45 or other data acquisition system. In other embodiments, the strain gauges 48 can be coupled to internal wiring (not shown) routed through the lumen 22 and the handle 14.

The strain gauges 48 can independently measure bending forces (and, thus, can be uniaxial or rosette gauges). For each pair of in-line strain gauges, because the distance between D1 and D2 can be known, known loads at distances offset from both strain gauges 48 can be used to calibrate their readings. These known loads and readings can be used to create calibration curves (e.g., of strain versus applied moment). As a result, a calibration curve slope can be determined, for each strain gauge 48, in terms of strain output per unit Newton-meter (Nm) of applied bending. Notably, the curves will be different for the in-line strain gauges because of their different distances from the applied loads. Once calibrated, for any subsequent unknown force applied to the body 12 and offset from the strain gauges 48, even though its location is initially unknown, the new gauge readings and the calibrated slopes can be used to mathematically determine the force magnitude (in Newtons) as well as the location of the net force.

By way of example, when an unknown force F is applied to the body 12 at an unknown distance from the in-line strain gauges 48 (e.g., at unknown distance $x_1$ from the first strain gauge 48 and unknown distance $x_2$ from the second strain gauge 48), the gauge readings can be used, with the calibration curves discussed above, to determine respective bending moments $M_1$, $M_2$ at each strain gauge 48. The bending moments may thus be defined as $M_1=x_1F$ and $M_2=x_2F$. Force may be calculated as $F=(M_1-M_2)/d$, and the distance from the point d to the force application point $x_1=M_1d/(M_2-M_1)$, where $d=(x_2-x_1)$ is the known distance between the strain gauges 48. Accordingly, because the moments $M_1$, $M_2$ can be obtained using the calibration curves and the distance between strain gauges 48 is known, the distance from the strain gauges to the point of applied force can be calculated.

Additionally, in some embodiments, the in-line strain gauges 48 can be placed around a circumference of the body 12 to obtain horizontal and vertical components of the applied force. For example, in-line strain gauges 48 can be placed at points A and B in the example shown in FIG. 15, which would provide a first component (e.g., a vertical component) of a force acting on the body 12 and in-line strain gauges 48 can be placed at point C and a point opposite point C in the example shown in FIG. 15, which would provide a second component (e.g., a horizontal component) of the force acting on the body 12. By obtaining strain measurements in both component directions, the resultant radial force magnitude can be determined.

Thus, the computer system 45 can obtain readings from the in-line strain gauges 48, calculate force applied by the multifunctional medical device 10 against a tissue based on measurements from the strain gauges 48 (independent of the location of applied force), and provide feedback to the surgeon operating the device 10 (either through the computer system 45 or a separately connected indicator 43) based on the calculated force.

Furthermore, generally, any of the above-described embodiments of the multipurpose medical device 10 can be in communication with one or more computer systems 45. For example, the device 10 can be in wired or wireless communication with the computer systems 45. In some embodiments, the computer systems 45 may comprise elements such as a picture archiving and communication system (PACS system) or one or more electronic health records. Moreover, while the sensing system 30 has been described to be in communication with the computer system 45, in some embodiments, one or more of the other functional systems of the multipurpose medical device 10 can be in communication with the computer systems 45. For example, the suction system 24, the sensing system 30, the irrigation system 28, and/or any other function system can be in communication with the computer systems 45 in some embodiments. As such, data can be gleaned from the operations of these systems, e.g., from inputs to the computer system 45, for long-term record keeping in the one or more computer systems 45. This data can be used to determine force application and provide feedback, as described above, and also can be used in the care of the patient and/or to understand the activities taken by the surgeon during the procedure. In some aspects, the data can also be used to aid in clinical and medicolegal issues that may arise as a result of the surgical procedure.

When taken together, the different systems of the multipurpose medical device 10 can provide significant benefits over conventional devices. For example, by have a single device that includes the suction system 24, the stimulation system 26, the irrigation system 28, the lighting system 29, and/or the sensing system 30, the device 10 provides a combination of functionalities that the surgeon can use to effectively and efficiently perform a surgical procedure (e.g., cranial surgeries, spinal surgeries, such as minimally invasive spine surgery, peripheral nerve surgeries, or other medical procedures). Specifically, by combining one or more of these benefits into one device, the time required to change instruments during the procedure can be reduced, which also reduces the total amount of time of the procedure. These reductions in instrument changes and overall time of procedure can lead to improved patient safety (e.g., via at least increased surgeon concentration, minimized clutter, and/or minimized infection risk). Moreover, by including the retraction functionality and the sensing system 30 with at least one sensor 42, the multifunctional medical device 10 can quantitatively monitor tool-tissue interactions in real-time and provide visual, auditory, and/or haptic feedback to the healthcare provider. As a result, the risks of retraction overload and unexpected retraction-based damage to the brain and nerves can be reduced. In addition, this feedback mechanism can also be used to train residents and surgeons to apply the correct amount of retractive force during a procedure, thus decreasing learning curves and increasing patient safety.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A multipurpose medical device configured to be used by a user during a medical procedure, the device comprising:
   a handle;
   a substantially cylindrical unitary body operatively coupled to the handle and including a lumen extending through a length of the body, at least a portion of the body being configured to operate as a retractor during the medical procedure;
   a suction system including a suction channel disposed within the lumen;
   a sensing system including a plurality of in-line sensors coupled to the body and configured to sense a retraction force against the body during the medical procedure independently from a location of application of the force; and
   an indicator configured to provide feedback to the user based on the sensed retraction force,
   wherein the sensing system includes a plurality of pairs of gauges arranged around a circumference of the body, each of the plurality of pairs including first and second in-line gauges arranged in an axial direction of the body, the first and second in-line gauges being coupled to the body at a first location and at a second location, respectively, such as to be separated from one another by a known distance, and
   wherein the sensing system is configured to determine distances between the location of application of said force and the first and second locations.

2. The device of claim 1, wherein the indicator comprises at least one of a visual indicator, a haptic indicator, and an auditory indicator.

3. The device of claim 1, wherein the indicator is configured to provide different feedback to the user based on a level of retraction force sensed by the sensing system.

4. The device of claim 1, wherein the indicator is configured to provide feedback to the user upon a detection of a sensed retraction force between about 0.3 Newtons to about 1.5 Newtons.

5. The device of claim 1, wherein the plurality of in-line sensors comprises a plurality of in-line pressure sensors coupled to the body.

6. The device of claim 5, wherein each of the pressure sensors comprises a uniaxial strain gauge configured to sense a bending force along the body.

7. The device of claim 5, wherein each of the pressure sensors comprises a rosette strain gauge configured to sense bending and shear forces along the body.

8. The device of claim 5,
   wherein the sensing system is configured to sense the retraction force against the body based on predetermined calibration curves associated with the plurality of in-line pressure sensors.

9. The device of claim 1, wherein the body comprises one of a substantially linear configuration and an at least partially angled configuration relative to the handle.

10. The device of claim 1, wherein the suction system further comprises a suction control aperture disposed through at least a portion of the handle, the suction control aperture being in operative fluid communication with the suction channel and configured to control suction applied through the suction channel, and wherein the suction channel extends axially through the lumen.

11. The device of claim 1 and further comprising a computer system in communication with the sensing system and configured to receive data from the sensing system relating to the sensed retraction force.

12. The device of claim 1, wherein the body further supports at least a portion of one of a stimulation system, a lighting system and an irrigation system.

13. The device of claim 1, wherein the body further supports at least a portion of a stimulation system, wherein the stimulation system comprises a stimulation channel at least partially disposed within the lumen and a stimulator tip disposed at a distal end of the body, the stimulator tip configured to provide electrical current to tissue during the medical procedure.

14. The device of claim 1 wherein the body comprises an outer diameter between about two millimeters and about five millimeters.

15. A method of performing a surgical procedure within a surgical field, the method comprising:
   providing a multipurpose medical device comprising a substantially cylindrical unitary body configured to operate as a retractor, an inner surface of the body comprising a lumen, a suction system at least partially disposed within the lumen, and a sensing system at least partially supported by the body;
   positioning the device within the surgical field;
   retracting one or more tissues within the surgical field using the device;
   sensing force exerted against the device during retraction, independent from a location of application of the force, using a plurality of pairs of gauges of the sensing system arranged around a circumference of the body, each of the plurality of pairs including first and second in- line gauges arranged in an axial direction of the body, the first and second in-line gauges being coupled to the body at a first location and at a second location, respectively, such as to be separated from one another by a known distance;
   the sensing system determining distances between the location of application of said force and the first and second locations; and
   providing an indication via an indicator of the sensing system if the sensed force exceeds a predetermined threshold.

16. The method of claim 15, wherein the device further comprises a stimulation system at least partially disposed within the lumen; and further comprising assessing proximity to one or more nerves in the surgical field by providing an electrical current through the stimulation system.

17. The method of claim 15, wherein the device further comprises an irrigation system at least partially disposed within the lumen; and further comprising irrigating at least a portion of the surgical field using the irrigation system.

18. The method of claim 15 and further comprising further retracting one or more tissues within the surgical field using an inflatable member supported by the body.

19. The method of claim 15, wherein providing the indication if the sensed force exceeds the predetermined threshold comprises providing at least one of an auditory indication, a visual indication, and a haptic indication.

20. The method of claim 15, wherein the surgical procedure is selected from the group consisting of peripheral nerve surgery, spine surgery, and cranial surgery.

* * * * *